(12) United States Patent
Andregg et al.

(10) Patent No.: US 8,153,438 B2
(45) Date of Patent: Apr. 10, 2012

(54) SEQUENCING NUCLEIC ACID POLYMERS WITH ELECTRON MICROSCOPY

(75) Inventors: William Andregg, Los Altos Hills, CA (US); Michael Andregg, Los Altos Hills, CA (US)

(73) Assignee: Halcyon Molecular, Redwood City, CA (US)

( * ) Notice: Subject to any disclaimer, the term of this patent is extended or adjusted under 35 U.S.C. 154(b) by 78 days.

(21) Appl. No.: 12/753,693

(22) Filed: Apr. 2, 2010

(65) Prior Publication Data

US 2010/0267152 A1    Oct. 21, 2010

Related U.S. Application Data

(63) Continuation of application No. PCT/US2008/078986, filed on Oct. 6, 2008.

(60) Provisional application No. 60/997,427, filed on Oct. 4, 2007, provisional application No. 61/132,960, filed on Jun. 23, 2008.

(51) Int. Cl.
*G01N 1/28* (2006.01)

(52) U.S. Cl. .................. 436/94; 436/149; 436/171

(58) Field of Classification Search .......... 436/94, 436/149, 171; 435/6, 287.2; 702/20
See application file for complete search history.

(56) References Cited

U.S. PATENT DOCUMENTS

| | | | |
|---|---|---|---|
| 4,689,295 A | 8/1987 | Taber et al. | |
| 5,106,729 A | 4/1992 | Lindsay et al. | |
| 5,447,841 A | 9/1995 | Gray et al. | |
| 5,470,707 A | 11/1995 | Sasaki et al. | |
| 5,472,881 A | 12/1995 | Beebe et al. | |
| 5,601,982 A | 2/1997 | Sargent et al. | |
| 5,674,743 A | 10/1997 | Ulmer | |
| 5,789,161 A | 8/1998 | Morrison et al. | |
| 5,800,992 A | 9/1998 | Fodor et al. | |
| 5,843,650 A | 12/1998 | Sergev | |
| 5,871,912 A | 2/1999 | Heym et al. | |
| 5,903,085 A | 5/1999 | Karam | |
| 6,210,891 B1 | 4/2001 | Nyren et al. | |
| 6,221,581 B1 | 4/2001 | Englehardt et al. | |
| 6,342,354 B1 | 1/2002 | Chartrand et al. | |
| 6,348,313 B1 | 2/2002 | Sibson | |
| 6,582,921 B2 | 6/2003 | Mirkin et al. | |
| 6,604,052 B1 | 8/2003 | Jensen et al. | |
| 6,713,263 B2 | 3/2004 | Schwartz | |
| 6,743,584 B1 | 6/2004 | Bub et al. | |
| 6,852,487 B1 | 2/2005 | Barany et al. | |
| 6,875,984 B2 | 4/2005 | Kakibayashi et al. | |
| 7,083,917 B2 | 8/2006 | Barany et al. | |

(Continued)

FOREIGN PATENT DOCUMENTS

DE    19937512 A1 *   2/2001

OTHER PUBLICATIONS

Machine Translation of DE 199 37 512 A1, obtained by the examienr on Aug. 15, 2011 from espacenet.com.*

(Continued)

*Primary Examiner* — Yelena G Gakh
*Assistant Examiner* — Christopher A Hixson
(74) *Attorney, Agent, or Firm* — Hogan Lovells US LLP

(57) ABSTRACT

This invention relates to using an electron microscope to sequence by direct inspection of labeled, stretched DNA. This method will have higher accuracy, lower cost, and longer read length than current DNA sequencing methods.

37 Claims, 21 Drawing Sheets

U.S. PATENT DOCUMENTS

| | | |
|---|---|---|
| 7,101,667 B2 | 9/2006 | Imperiali et al. |
| 7,211,390 B2 | 5/2007 | Rothberg et al. |
| 7,236,889 B2 | 6/2007 | Shirasaki et al. |
| 7,244,559 B2 | 7/2007 | Rothberg et al. |
| 7,288,379 B2 | 10/2007 | Glover, III et al. |
| 7,291,467 B2 | 11/2007 | Glover, III et al. |
| 7,291,468 B2 | 11/2007 | Glover, III et al. |
| 7,294,460 B2 | 11/2007 | Pompon et al. |
| 7,312,039 B2 | 12/2007 | Barany et al. |
| 7,332,284 B2 | 2/2008 | Nagayama |
| 7,332,285 B2 | 2/2008 | Barany et al. |
| 7,364,858 B2 | 4/2008 | Barany et al. |
| 7,381,529 B2 | 6/2008 | Yamakawa et al. |
| 7,419,833 B2 | 9/2008 | Nagayama |
| 7,429,453 B2 | 9/2008 | Barany et al. |
| 7,442,931 B2 | 10/2008 | Zewail et al. |
| 7,455,965 B2 | 11/2008 | Barany et al. |
| 7,553,621 B2 | 6/2009 | Ginot et al. |
| 7,556,924 B2 | 7/2009 | Barany et al. |
| 7,604,942 B2 | 10/2009 | Glover, III et al. |
| 7,604,943 B2 | 10/2009 | Glover, III et al. |
| 7,618,778 B2 | 11/2009 | Kaufman |
| 2002/0086317 A1 | 7/2002 | Nagayama |
| 2002/0168642 A1 | 11/2002 | Drukier |
| 2002/0182626 A1 | 12/2002 | Tuse |
| 2003/0022182 A1 | 1/2003 | Barany et al. |
| 2004/0038261 A1* | 2/2004 | Nagayama ............ 435/6 |
| 2004/0081985 A1 | 4/2004 | Ciccolella et al. |
| 2004/0086885 A1 | 5/2004 | Lee et al. |
| 2004/0248144 A1 | 12/2004 | Mir |
| 2004/0259141 A1 | 12/2004 | Barany et al. |
| 2005/0009055 A1 | 1/2005 | Ciccolella et al. |
| 2005/0042633 A1 | 2/2005 | Williams |
| 2005/0147977 A1 | 7/2005 | Koo et al. |
| 2005/0244863 A1 | 11/2005 | Mir |
| 2006/0003437 A1 | 1/2006 | Fujihara et al. |
| 2006/0024717 A1 | 2/2006 | Glover, III et al. |
| 2006/0024718 A1 | 2/2006 | Glover, III et al. |
| 2006/0029957 A1 | 2/2006 | Glover, III et al. |
| 2006/0060778 A1 | 3/2006 | Fujihara et al. |
| 2006/0154274 A1 | 7/2006 | Finkelstein et al. |
| 2006/0204965 A1* | 9/2006 | Higuchi et al. ............ 435/6 |
| 2006/0287833 A1 | 12/2006 | Yakhini |
| 2007/0015175 A1 | 1/2007 | Kumar et al. |
| 2007/0054306 A1 | 3/2007 | Barany et al. |
| 2007/0072187 A1 | 3/2007 | Blok et al. |
| 2007/0128610 A1 | 6/2007 | Buzby |
| 2007/0134699 A1* | 6/2007 | Glover et al. ............ 435/6 |
| 2007/0172869 A1 | 7/2007 | Hardin et al. |
| 2007/0190326 A1 | 8/2007 | Perry et al. |
| 2007/0190557 A1 | 8/2007 | Glover, III et al. |
| 2008/0131899 A1 | 6/2008 | Landergren et al. |
| 2008/0199871 A1 | 8/2008 | Glover |
| 2008/0227095 A1 | 9/2008 | Glover |
| 2009/0018029 A1 | 1/2009 | Miao et al. |
| 2009/0029370 A1 | 1/2009 | Broude et al. |
| 2009/0029383 A1 | 1/2009 | Densham |
| 2009/0031444 A1 | 1/2009 | Wittich et al. |
| 2009/0092970 A1 | 4/2009 | Williams |
| 2009/0111115 A1 | 4/2009 | Drmanac et al. |
| 2009/0130686 A1 | 5/2009 | Hausmann et al. |
| 2009/0162860 A1 | 6/2009 | Ikuta et al. |
| 2009/0181387 A1 | 7/2009 | Maes et al. |
| 2009/0208960 A1 | 8/2009 | Kelly et al. |
| 2009/0208965 A1 | 8/2009 | Tafas et al. |
| 2009/0215643 A1 | 8/2009 | Aurich-Costa et al. |
| 2009/0236521 A1 | 9/2009 | Zewail et al. |
| 2009/0239215 A1 | 9/2009 | Derosier et al. |
| 2009/0305273 A1 | 12/2009 | Cao et al. |
| 2009/0306183 A1 | 12/2009 | Golemis et al. |
| 2010/0035254 A1 | 2/2010 | Williams |
| 2010/0105055 A1 | 4/2010 | Glover, III et al. |

OTHER PUBLICATIONS

Gupta, Pushpendra K. "Single-molecule DNA sequencing technologies for future genomics research." Trends in Biotechnology (2008) 26 602-611.*

Shendure, Jay et al. "Next-generation DNA sequencing." Nature Biotechnology (2008) 26 1135-1145.*

Guan, Jingliao et al. "Generating highly ordered DNA nanostrand arrays." PNAS (2005) 102 18321-18325.*

Michalet, Xavier et al. "Dynamic Molecular Combing: Stretching the Whole Human Genome for High-Resolution Studies." Science (1997) 277 1518-1523.*

Aoyama et al., "Elemental mapping of DNA chains by energy-filtering TEM" Journal of Electron Microscopy 52(3): 283-289 (2003).

Bartl et al., "Electron microscopic study of base sequence in nucleic acids VI. Guanine sites in yeast alanine transfer RNA" Micron (1970) 1:374-392.

Beer et al., "Determination of Base Sequence in Nucleic Acids with The Electron Microscope: Visibility of a Marker" Department of Biophysics, The Johns Hopkins University, Biochemistry: Moudrianakis and Beer (1962) pp. 409-416.

Beer et al., Electron Microscopy of Nucleic Acids Methods in Cancer Research, vol. 6 (1971) 283-309.

Beer et al., "Determination of Base Sequence in Nucleic Acids with the Electron Microscope. V. The Thymine-Specific Reactions of Osmium Textroxide with Deoxyribonucleic Acid and Its Components" Base Sequences by Electron Microscopy, vol. 5, No. 7, (1996).

Bensimon et al., "Alignment and Sensitive Detection of DNA by a Moving Interface" Science, vol. 265 (1994) pp. 2096-2098.

Bustamante et al., "Ten years of tension: single-molecule DNA mechanics" Nature, vol. 421 (2003) pp. 423-427.

Cole et al, "Molecular Microscopy of Labeled Polynucleotides: Stability of Osmium Atoms" J. Mol. Biol. (1977) 117, 387-400.

Crewe, "Direct Imaging of Single Atoms and Molecules Using the STEM" Chemica Scripta (1978) 14, 17-20.

Erickson et al., Visibility of Single Nucleic Acid Molecules and Implications for the Study of Nucleotide Sequence Biophysics Department, Johns Hopkins University, Fourth European Regional Conference on Electron Microscopy (1968) pp. 87-88.

Fujiyoshi et al., "Direct Imaging of a Double-Strand DNA Molecule" Ultramicroscopy 7 (1981) pp. 189-192.

Isaacson et al., "The preparation and observation of biological specimens for the high resolution scanning transmission electron microscope" Scanning Electron Microscopy (1974) 8 pp.

Kato et al., "Electron microscopic imaging of supercoiled DNA containing highly biased sequence" Nucleic Acids Research Supplement No. 1, Oxford Press (2001) 157-158.

Koller et al., Electron Microscopy of Selectively Stained Molecules Cytobilogie vol. 4, No. 3 (1971) pp. 369-408.

Kozinski et al., "Effect of Concentration on the Formation of Molecular Hybrids from T4 DNA" Department of Biology and Biophysics, Johns Hopkins University, Biophysical Journal, vol. 2 (1962).

Langmore et al., "Progress towards the sequencing of DNA by electron microscopy" Thirty-Second Annual EMSA Meeting (N.D.) pp. 376-377.

Moudrianakis et al., "Base Sequence Determination in Nucleic Acids with the Electron Microscope, III. Chemistry and Microscopy of Guanine-labeled DNA" Department of Biophysics, The Johns Hopkins University, Biochemistry: Moudrianakis and Beer, vol. 53 (1965) pp. 564-571.

Ottensmeyer, "Molecular Structure Determination by High Resolution Electron Microscopy" Ann. Rev. Biophys. Bioeng. (1979) 8:129-144.

Ottensmeyer, Scattered Electrons in Microscopy and Microanalysis Science, vol. 215, No. 4532 (1982) pp. 461-466.

Takai et al., "Molecular-scale imaging of unstained deoxyribonucleic acid fibers by phase transmission electron microscopy" Applied Physics Letters 89 (2006) 3 pp.

Tanaka et al., "Electron Microscope Images of Mercury Atoms Bound to DNA Filament" Ultramicroscopy 1 (1975) 7-14.

Whiting et al., Heavy Atoms in Model Compounds and Nucleic Acids Imaged by Dark Field Transmission Electron Microscopy J. Mol. Biol (1972) 67, 173-181.

Whiting, "Studies of Nucleic Acid Sequences by Dark Field Electron Microscopy" Thesis, Universoty of Toronto (1975) 120 pp.

* cited by examiner

Panel I Panel II

GRID

SEQUENCING NUCLEIC ACID POLYMERS WITH ELECTRON MICROSCOPY

CROSS-REFERENCE TO RELATED APPLICATIONS

This application claims priority to U.S. Provisional Application No. 60/997,427, filed Oct. 4, 2007, and U.S. Provisional Application No. 61/132,960, filed Jun. 23, 2008, the disclosures of which are expressly incorporated herein by reference in their entirety.

FIELD OF THE INVENTION

The invention relates to methods of sequencing nucleic acids.

BACKGROUND OF THE INVENTION

Current DNA sequencing is done mostly by Sanger methods and other sequencing-by-synthesis methods. These methods suffer from high cost, short read lengths, and insufficient throughput.

Sequencing by electron microscopy has also been explored. The idea of sequencing by electron microscopy is not new. It was proposed by Richard Feynman only six years after the structure of DNA was discovered. However, it has never been successfully used to generate meaningful sequence information.

The transmission electron microscope (TEM) works by sending an electron beam through a sample and onto a detector or screen. Portions in the sample impede or deflect the beam, so that the pattern of electrons reaching the detector forms an image. In most situations, atoms of low atomic number (Z) produce very little contrast and are essentially invisible in the electron microscope. Ordinary DNA, comprising low-Z hydrogen, carbon, nitrogen, oxygen, and phosphorus atoms shows almost no contrast in an electron microscope and is almost impossible to see against a supporting background. To visualize DNA using current electron microscopy techniques, the bases may be labeled with high-Z atoms or otherwise rendered detectable by TEM.

The first serious work on sequencing by electron microscopy was done by Beer, M. and Moudrianakis, E. N., 48(3) PNAS 409-416 (1962). His initial work focused on heavy atom labels for DNA and also attempting to visualize heavy atoms in the electron microscope. Later work, and probably the best other work to date, was done by Whiting and Ottensmeyer. It was reported by Ottensmeyer:

> Heavy atom markers for thymine and adenine and guanine were developed and tried on model sequences, only to indicate that although the electron microscope and the chemistry were no longer major obstacles, specimen preparation was. The uncontrollable placing of a marked single-stranded nucleic acid polymer on the specimen support resulted in a rather non-uniform base-to-base spacing. Therefore an easy and accurate reading from a single molecule was not possible." Ottensmeyer, F. P. (1979). "Molecular Structure Determination by High Resolution Electron Microscopy." *Ann. Rev. Biophys. Bioeng.* 9129: 129-144. (Internal references omitted.)

There is great biomedical importance to having the ability to rapidly sequence individual genomes and other sequences, and as described above, improved methods are needed.

BRIEF SUMMARY OF THE INVENTION

The invention provides methods for using an electron microscope to sequence by direct inspection of labeled, stretched nucleic acid, such as DNA. The methods, devices, and compositions of the invention allow controllable placement of a nucleic acid on a substrate, so that there is consistent base-to-base spacing, allowing for accurate nucleic acid sequencing information to be obtained using electron microscopy. The invention may be implemented in a number of ways.

According to one aspect of the invention, a method for obtaining sequence information of a DNA polymer strand may include providing a solution comprising a DNA polymer strand, where the DNA polymer strand has been treated such that a plurality of DNA bases have been labeled with an contrast agent with base specificity or base selectivity, introducing a DNA binding tool into the solution and binding a section of the DNA polymer onto the tool, removing the tool from the solution, stretching the labeled DNA polymer strand into space such that the labeled DNA polymer strand is suspended between an air/solvent interface and the tool, depositing the stretched labeled DNA polymer strand onto a substrate, imaging the labeled DNA d polymer strand using electron microscopy such that positions of labeled and unlabeled bases are determined, and correlating the positions of labeled and unlabeled bases with the sequence of the DNA polymer.

The method may further include denaturing the DNA strand to generate single stranded DNA prior to labeling with the contrast agent. The denaturing step is carried out by thermal denaturation or chemical denaturation. The method may also include depositing a layer of carbon on top of the labeled DNA polymer strand attached to the substrate prior to said imaging step. The method may also include labeling multiple strands from a DNA polymer sample with different labels and compiling the data obtained from imaging the multiple strands of the DNA polymer to obtain the complete sequence information.

The DNA may be high molecular weight DNA having greater than about 100 kb. The stretching step may result in consistent base-to-base spacing in the DNA polymer strand. The base-to-base spacing between the bases may be is in a range of about 3 Å to about 7 Å, and specifically be about 5 Å. The DNA polymer strand may be stretched to a length of at least about 2 μm.

Only a subset of bases of the DNA polymer strand may be labeled. The subset of bases comprises thymines and cytosines. The subset of bases comprises adenine and guanine.

The tool may be a needle such that a tip of the needle has been functionalized with a first coating that binds to a DNA polymer strand. The needle may be fabricated from glass, gold, tungsten, PMMA, polystyrene, PVC, or silicon. The coating may be a compound such as PMMA, polystyrene, PVB, and oligonucleotides. The needle may be functionalized with a second coating that does not bind to nucleic acids. The second coating may be at least one of octanethiol, hexanethiol, nonanethiol, decanethiol, and septanethiol. The tip of the needle has a radius of curvature that is less than about 200 nm. The needle may be moved into and out of the solution at a rate in a range of about 1 nanometers/second to about 100 meters/second. Specifically, the needle may be moved into the solution at a depth having a range of about 1 Å to about 20 μm.

The contrast agent may be a high-Z atom labeling compound. The high-Z atom may be Os-bipy, mercuric acetate, and platinum dimethylsulfoxide. The contrast agent may be a high-Z atom cluster label.

The DNA polymer strand may be attached to a substrate by employing shelf threading. The DNA polymer strand may be attached to either a support substrate or an imaging substrate. The DNA polymer strand may be attached to a support substrate by employing shelf threading followed by transferring the labeled DNA polymer strand on the support substrate to an imaging substrate by employing transfer printing. The DNA polymer strand may be attached to a support substrate by employing gap threading following by transferring the labeled DNA polymer strand on the support substrate to an imaging substrate by employing swipe printing. The DNA polymer strands may be a plurality of DNA polymer strands and may be positioned as an array of parallel strands on a substrate. The stretched labeled DNA polymer strand may be single stranded.

According to one aspect of the invention, a method for obtaining a nucleic acid sequence information may include determining by electron microscopy the positions of labeled and unlabeled bases of a nucleic acid strand within a region of at least 1000 contiguous bases of each of a plurality of labeled nucleic acid strand are determined. Specifically, the positions of at 1000 contiguous bases of a nucleic acid strand may be determined, and more specifically, the positions of at 10,000 contiguous bases of a nucleic acid strand may be determined. The positions of labeled and unlabeled bases of at least about 20 individual strands may be determined, the positions of at least about 100 multiple strands may be determined, the positions of at least about 5,000 multiple strands may be determined, and the positions of at least about 10,000 multiple strands may be determined. The positions may be determined for differently labeled nucleic acid polymer strands from the same sample. The positions may be determined for differently labeled nucleic acid polymer strands of at least 200 contiguous bases, of at least 500 contiguous bases, of at least 1000 contiguous bases, or of at least 10,000 contiguous bases.

The nucleic acid sequence may be obtained at a rate at least 1,000 bases/second. The nucleic acid strand may have a length of at least about 100 μm when extended. The nucleic acid may have base-to-base spacing in a range of 3 Å to about 7 Å between the bases, and specifically, about 5 Å. The nucleic acid sequence may be a DNA sequence.

According to another aspect of the invention, an article of manufacture may include a liquid having a plurality of nucleic acid polymer strands, a tool, and a single nucleic acid polymer strand having a first end in the liquid and a second end attached to the tool, where at least a portion of the single nucleic acid polymer strand is suspended in space between the tool and the liquid. The bases of the nucleic acid polymer strand may be extended such that there is consistent base-to-base spacing of the bases. The base-to-base spacing may be in a range of 3 Å to about 7 Å between the bases. The nucleic acid polymer strand may be extended such that the strands are linear.

According to yet another aspect of the invention, an article of manufacture may include a solid planar substrate, and at least one elongated nucleic acid polymer strand disposed on the planar substrate. The least one elongated nucleic acid polymer strand may have consistent base-to-base spacing over a length of about 1000 base pairs. The article of manufacture may further include a film disposed on top of the at least one elongated nucleic acid polymer such that the at least one elongated nucleic acid polymer is sandwiched between the planar substrate and the film. The film may be composed of a carbon or low Z-element. The planar substrate may be composed of a material such as PDMS, carbon, boron, lithium, hydrogen, beryllium, aluminum, nitrides, nitride oxides, and combinations thereof.

The base-to-base spacing of the at least one elongated nucleic acid strand may be in a range of 3 Å to about 7 Å. The plurality of elongated nucleic acid strand may be substantially parallel to one another. The plurality of elongated nucleic acid strand may include about $1 \times 10^6$ nucleic acid strands. The at least one elongated nucleic acid strand may be stretched to a length of at least about 2 μm. The at least one nucleic acid polymer acid strand may be labeled with at least one Z-labeling compound. The Z-labeling compound may be a high-Z atom labeling compound such as Os-bipy, mercuric acetate, platinum dimethylsulfoxide, or cluster labeling.

According to a further aspect of the invention, a method for sequencing at least 200 contiguous bases of a nucleic acid strand using electron microscopy may include labeling a plurality of nucleic acid strands with at least one Z-labeling compound, binding a single labeled nucleic acid strand from a solution containing a plurality of labeled nucleic acid strands onto a tool, stretching the single labeled nucleic acid strand into space such that the single labeled strand of nucleic acid is suspended between an air/solvent interface and a tip of the tool, attaching the stretched labeled nucleic acid to a substrate, and imaging the labeled nucleic acid strand using electron microscopy.

The method may further include pretreating a solution containing a plurality of nucleic acid strands with bisulfite to convert unmethylated cytosine bases to uracil bases prior to the labeling step. The method may also include denaturing a plurality of nucleic acid strands to generate single stranded nucleic acids prior to the labeling step. The denaturing step may be carried out by thermal denaturation or chemical denaturation. The method may also include depositing a layer of carbon on top of the labeled nucleic acid strand attached to the substrate prior to the imaging step.

The nucleic acid may be high molecular weight DNA. The stretching step results in consistent base-to-base spacing in the nucleic acid strand. The base-to-base spacing and the label-to-label spacing may be in a range of about 3 Å to about 7 Å, and specifically may be 5 Å. The nucleic acid strand may be stretched to a length of at least about 25 μm. Only a subset of bases of the nucleic acid strand are labeled. The subset of bases may include thymines and cytosines. The subset of bases may include adenine and guanine.

The tool may be a needle such that a tip of the needle has been functionalized with a first coating that binds to a nucleic acid strand. The needle may be fabricated from a material such as glass, gold, tungsten, polymethyl methylacrylate (PMMA), polystyrene, PVC, and silicon. The coating may be a compound such as PMMA, polystyrene, PVB, and oligonucleotides. The needle may be functionalized with a second coating that does not bind to nucleic acids. The second coating may be a compound such as octanethiol, hexanethiol, nonanethiol, decanethiol, and septanethiol.

The tip of the needle may have a diameter that is less than about 200 nm. The needle may be moved into and out of the solution at a rate in a range of about 1 nanometers/second to about 100 meters/second. The needle may be moved into the solution at a depth having a range of about 0 nm to about 20 μm.

The at least one labeling compound may be a high-Z atom labeling compound. The high-Z atom may be one or more compounds such as Os-bipy, mercuric acetate, and platinum dimethylsulfoxide. The at least one labeling compound may be a high-Z atom cluster label.

The attaching step may include attaching at least one labeled nucleic acid strand to an imaging substrate by employing shelf threading. The attaching step may include attaching at least one labeled nucleic acid strand to a support substrate by employing shelf threading followed by transferring the at least one labeled nucleic acid strand on the support substrate to an imaging substrate by employing transfer printing. The attaching step may include attaching at least one labeled nucleic acid strand to a support substrate by employing gap threading. The attaching step may include attaching at least one labeled nucleic acid strand to a support substrate by employing gap threading following by transferring the at least one labeled nucleic acid strand on the support substrate to an imaging substrate by employing swipe printing.

According to an even further aspect of the invention, a method for the controlled placement of at least one nucleic acid strand onto a substrate may include providing a solution containing a plurality of nucleic acid strands, inserting a tip of a needle into the solution, pulling the tip of the needle out of the solution containing a plurality of nucleic acid strands, where the tip of the needle has been functionalized with a first coating that binds to nucleic acids, stretching the nucleic acid strand into empty space such that the single strand of nucleic acid is suspended between an air/solvent interface and each tip of the needle, and attaching at least one stretched nucleic acid strand to a substrate. The nucleic acid is high molecular weight DNA.

The needle may be fabricated from a material such as glass, gold, tungsten, PMMA, polystyrene, PVC, and silicon. The first coating may be a compound such as PMMA, polystyrene, PVB, and oligonucleotides. The needle may be functionalized with a second coating that does not bind to nucleic acids. The second coating may be a compound such as octanethiol, hexanethiol, nonanethiol, decanethiol, and septanethiol.

The tip of the needle may have a radius of curvature that is less than about 200 nm. The tip of the needle may be moved into and pulled out of the solution at a rate of about 1 nm/s to about 100 m/s. The tip of the needle may be moved into the solution at a depth having a range of about 10 nm to about 20 μm. The needle may be placed on a single nanopositioner-driven support. A plurality of needles may be inserted into the solution simultaneously with the nanopositioner driven support.

The stretching step may result in consistent base-to-base spacing in the nucleic acid strand. The base-to-base spacing may be in a range of about 3 Å to about 7 Å. The base-to-base spacing and the label-to-label spacing may be about 5 Å. The nucleic acid may be stretched to a length of about 100 μm.

The at least two nucleic acid strands attached to the substrate are oriented substantially parallel to each other. The attaching step may include employing shelf threading to attach the at least one nucleic acid strand to the substrate. The attaching step may include using gap threading to attach the at least one nucleic acid strand to the substrate. The substrate may be an imaging substrate. The substrate in said attaching step may be a support substrate.

According to another aspect of the invention, a method for analyzing a nucleic acid sequence stored in a memory, where the sequence was determined by labeling a plurality of nucleic acid strands with at least one labeling compound, binding a single labeled nucleic acid strand from a solution containing a plurality of labeled nucleic acid strands onto a tool, stretching the single labeled nucleic acid strand into space such that the single labeled strand of nucleic acid is suspended between an air/solvent interface and a tip of the tool, attaching the stretched labeled nucleic acid to a substrate, and imaging the labeled nucleic acid strand using electron microscopy. The nucleic acid sequence is a genomic sequence of a human subject.

The analyzing may include determining at least one of the presence or absence of one or more single nucleotide polymorphisms, copy number, variants, indels, rearrangements, or whole genome comparisons. The memory is a media selected from the group consisting of hard or floppy disks, optical media, compact disc (CD), digital video disc (DVD), semiconductor media, and flash memory.

According to a further aspect of the invention, a needle, may include a distal end, a proximal end, and a shaft extending between and in fluid communication with said distal proximal end and said proximal end, where the proximal end includes a tip member having a radius of curvature less than about 200 nm and where the tip member has been functionalized with a compound that binds to the end of a nucleic acid. The needle may be coated with a second compound that does not have an affinity for binding to a nucleic acid. The tip member may be functionalized with a compound such as PMMA, polystyrene, PVB, silanization, oligonucleotides, telomeres, and restriction site overhangs. The nucleic acid may be single stranded DNA. The needle may be composed of a compound such as glass, gold, tungsten, PMMA, polystyrene, PVC, and silicon. The needle may be disposed on a single nanopositioner-driven support.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention, are incorporated in and constitute a part of this specification, illustrate embodiments of the invention, and together with the detailed description serve to explain the principles of the invention. No attempt is made to show structural details of the invention in more detail than may be necessary for a fundamental understanding of the invention and various ways in which it may be practiced.

DETAILED DESCRIPTION OF THE INVENTION

Figure 1:
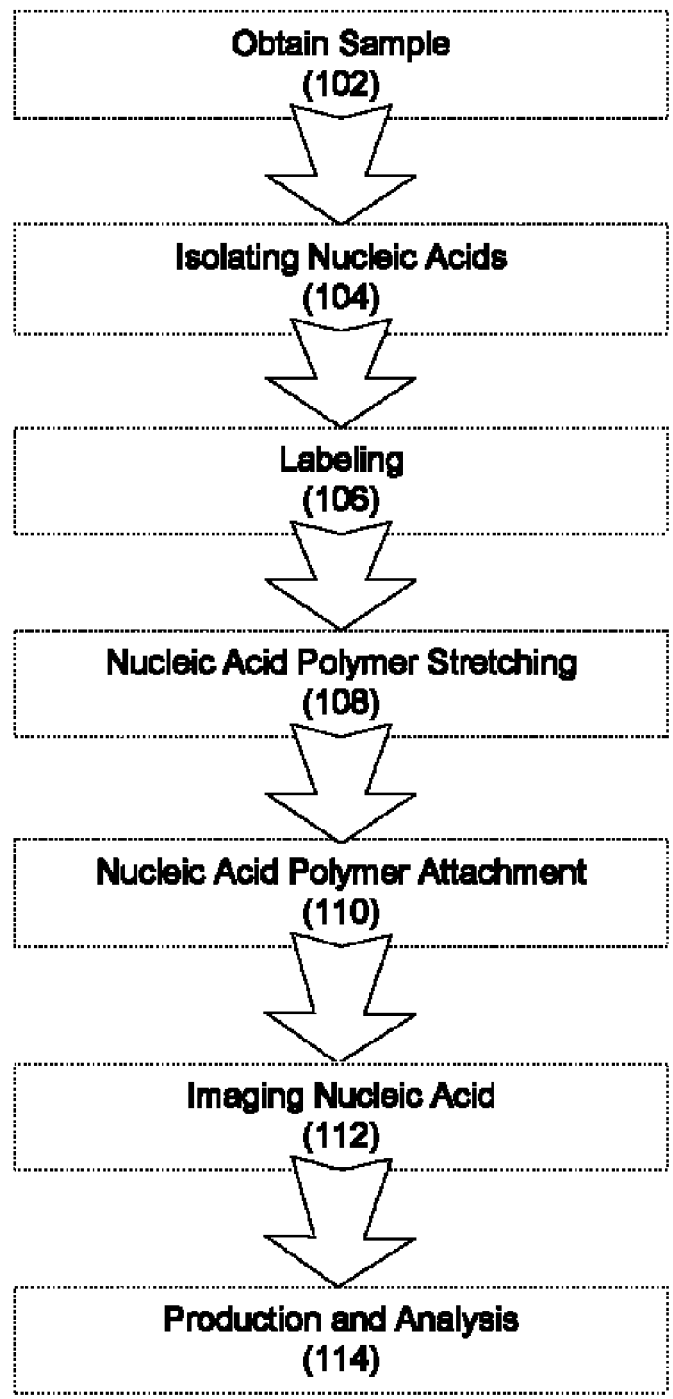
FIG. 1 is a flow chart illustrating a method for sequencing a nucleic acid accurately using electron microscopy according to principles of the invention.

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. It also is to be noted that, as used herein and in the appended claims, the singular forms "a," "an," and "the" include the plural reference unless the context clearly dictates otherwise. Thus, for example, a reference to "a molecule" is a reference to one or more molecule and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein.

Any numerical values recited herein include all values from the lower value to the upper value in increments of one unit provided that there is a separation of at least two units between any lower value and any higher value. As an example, if it is stated that the concentration of a component or value of a process variable such as, for example, size, angle size, pressure, time and the like, is, for example, from 1 to 90, specifically from 20 to 80, more specifically from 30 to 70, it is intended that values such as 15 to 85, 22 to 68, 43to 51, 30 to 32, etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Moreover, provided immediately below is a "Definition" section, where certain terms related to the invention are defined specifically. Particular methods, devices, and materials are described, although any methods and materials similar or equivalent to those described herein can be used in the practice or testing of the invention. All references referred to herein are incorporated by reference herein in their entirety.

DEFINITIONS

A is Adenine
C is Cytosine
G is Guanine
T is Thymine
U is Uracil
ssDNA is single stranded DNA
AFM is Atomic Force Microscope
CCD is Charge Coupled Device
CMOS is Complementary Metal Oxide Semiconductor
DMSO is Dimethyl Sulfoxide
EDTA is Ethylenediaminetetraacetic acid
HAADF is High Angle Annular Dark Field
IMPREST is Individual Molecule Placement Rapid Empty Space Threading
PFGE is pulsed field gel electrophoresis PFGE
Os-bipy is Osmium tetroxide 2,2'-bipyridine
PDMS is Polydimethylsiloxane
PLD-UHV is Pulsed Laser Deposition-Ultra High Vacuum
PMMA is Polymethyl methylacrylate
PMT is Photo Multiplier Tube
PVB is Polyvinyl butyral
SEM is Scanning Electron Microscopy
STEM is Scanning Transmission Electron Microscopy
TE is Tris EDTA TEM is Transmission Electron Microscopy UHV is Ultra High Vacuum The term "Z," as used herein refers to the number of protons in the nucleus of an atom, also known as atomic number. "High-Z" refers to an atomic number greater than then imaging thin-film, but for practical sequencing means higher than about 30, or preferably higher than about 70, or more preferably higher than about 90.

The term "consistent," as used herein, generally means that the spacing between the bases of the stretched nucleic acid strand is the relatively the same throughout the length of the stretched nucleic acid strand. The spacing "between" bases is generally the distance from center to center, or phosphate to phosphate. Bases are consistently spaced when in an electron microscopic image of the strand the order of labeled and unlabeled bases can be determined over a specified length, e.g., about 50 bases, about 100 bases, about 1000 bases, or about 10,000 bases.

The term "contiguous," as used herein, generally means that that the bases in a nucleic acid strand are all within a common boundary and are generally connecting without a break.

The term "consecutive," as used herein, generally means that the bases in the nucleic acid strand follow one another in uninterrupted succession or order.

The phrases "plurality of strands," "plurality of nucleic acid strands," "plurality of DNA strands," and the like refers to 2 strands, 5 strands, 10 strands, 100 strands, 1000 strands, and so on.

The term "support substrate," as used herein refers to any matrix to which the extended and/or stretched nucleic acid polymers can adhere.

The term "imaging substrate," as used herein refers to the substrate that will be used directly for electron microscopy imaging. The imaging substrate may be placed into the microscope and, optionally, support the imaging thin-film. The imaging substrate may include holey or lacey formvar mesh, other polymer meshes, thin silicon nitride films containing holes, and other suitable types of grids. The imaging substrate is generally thicker than the imaging thin-film but is needed to support the delicate imaging thin-film. The imaging substrate as used herein, may refer to the imaging thin-film and the support structure holding it or only the support substrate. See M. Hayat, *Principles and Techniques of Electron Microscopy: Biological Applications* 4th edition, which describes general methods in electron microscopy.

The term "imaging thin-film," as used herein refers to a thin layer of carbon, boron, lithium, hydrogen, beryllium, aluminum, or other low Z-elements and/or nitrides and oxides thereof, and any combination thereof. The layer may have a thickness in a range of about 0.2 nm to about 30 nm. The imaging thin-film may be supported on an imaging substrate or other surface.

The term "substantially parallel" generally refers to the geometrical concept of two straight lines never meeting. As used herein, substantially parallel refers to extended nucleic acid polymers that do not meet or cross over the area where sequence data is to be determined.

The term "nucleic acid," as used herein, includes oligonucleotides and polynucleotides, and to DNA or RNA of genomic, recombinant or synthetic origin which may be single- or double-stranded, and represent the sense or antisense strands, or to any DNA-like or RNA-like material, natural, recombinant, or synthetic in origin.

The term "complementary" as used herein, includes the natural hydrogen bonding of polynucleotides under permissive salt and temperature conditions by base-pairing. For example, the sequence "A-G-T" binds to the complementary sequence "T-C-A."

Complementarity between two single-stranded molecules may be partial, in which only some of the nucleic acids bind, or it may be complete when total complementarity exists between the single stranded molecules. The degree of complementarity between nucleic acid strands has significant effects of the efficiency and strength of hybridization between nucleic acid strands.

The term "sample," as used herein refers to biological material that contains nucleic acids, such as tissue or fluid from a human or animal including, but not limited to, plasma, serum, spinal fluid, lymph fluid, the external sections of the skin, respiratory, intestinal and genitourinary tracts, tears, saliva, blood cells, tumors, organs, tissues; as well as samples from plants, fungi, bacteria, pathogens and in vitro cell cultures. A sample may be obtained from any species that contain nucleic acids, phylogenetically encompassing all viruses, prokaryotes, and eukaryotes. A sample may also include nucleic acids that have been artificially synthesized using techniques known in the art such as solid-phase synthesis or synthesized in vitro using, for example, PCR.

The term "about," as used herein, is used to describe a range of values, applies to both the upper limit and lower limit of the range. For example, the phrase "ranges from about 10 to 100" has the same meaning as "ranges from about 10 to about 100." Moreover, when referring to distance, the term "about" generally means +/−10%. For example, the phrase "about 5 nm" means 5 nm+/−10%.

The terms "contrast agent," "label," or "labeling compound," as used herein generally refers to an atom, molecule, cluster, or material that has a higher atomic number (Z) and/or density and/or differential electron scattering than the imaging thin-film material and unlabeled DNA. The "contrast agent," "label," or "labeling compound" may be a compound of different contrast than the bases of the nucleic acid strand itself and is attached to the nucleic acid strand.

The term "cluster," as used herein, generally refers to chemical structure comprising two or more high-Z atoms, which is attached to a nucleic acid strand either base-selectively or base-specifically.

Overview

The invention generally relates to methods, devices and articles of manufacture for determining nucleic acid sequences using electron microscopy by direct inspection of labeled, stretched nucleic acids. In a particular embodiment, the invention relates to methods including controlled placement of a nucleic acid onto a substrate or support using a tool to pull out single strands of nucleic acid from a solution. The methods of the invention allow for greater accuracy, lower cost, and longer read lengths than current sequencing technology. For example, the sequencing methods of the invention allow accurate determination of at least about 20 consecutive nucleic acid bases using electron microscopy, preferably at least about 50 consecutive bases, more preferably at least about 1,000 consecutive bases, even more preferably at least about 10,000 consecutive bases, and even more preferably at least about 100,000 consecutive bases and even more preferably at least about 1,000,000 bases of a nucleic acid sample. "Consecutive bases" in this context refers the order of bases in the DNA starting material that is analyzed.

Using the methods of the invention it is also possible to generate sequence more rapidly than possible using synthetic methods. Methods of the invention (combined with high speed EM) may allow for imaging at least about 10,000 bases/second, and preferably at least about 100,000 bases/ second, and more preferable at least about 200,000 bases per second. For example, using TEM imaging, DNA strands arrayed according to the invention sample may be imaged at a high resolution rate of about 1 µm² per second. A 1 µm² area containing nucleic acid strands may be imaged in 1 second, correspond to an imaging rate of about 500,000 bases per second.

FIG. 1 is a flow chart illustrating a method for sequencing a nucleic acid accurately using electron microscopy according to principles of the invention. This figure is provided for illustration and is not intended to limit the invention. In step 102, a nucleic-acid containing sample is obtained from a subject containing a nucleic acid sequence(s) of interest. In step 104, using techniques known to those of skill in the art, the nucleic acid of interest is isolated from the sample. In step 106, specific bases of the isolated nucleic acid are labeled with, for example, high-Z atoms to generate a high-Z atom labeled nucleic acid polymer. In step 108, the nucleic acid polymer is stretched into empty space to ensure consistent base to base spacing of nucleotides. In step 110, nucleic acid polymers are attached to a support and laid out in a non-overlapping pattern (e.g., substantially parallel relative to each other). In step 112, the attached nucleic acid polymers are imaged by electron microscopy to determine the position of label along the polymer. The image is captured by a detector (e.g., CCD or CMOS camera, or PMT) and positions of the label are recorded, typically on a computer readable medium. In step 114, an algorithm is employed to use the spacing information to determine the base sequence information from the nucleic acid polymer. These steps are described in greater detail below.

Nucleic Acid Preparation

In step 104, the nucleic acid of interest may be isolated using methods well known in the art, with the choice of a specific method depending on the source, nature of nucleic acid, and similar factors. The nucleic acid of interest may be naturally occurring and/or of genomic origin, not of synthetic or recombinant origin, and may include oligonucleotides or polynucleotides either double stranded or single stranded form. Alternatively, the nucleic acid strand of interest may be of recombinant or synthetic origin, which may be single stranded or doubled stranded. In one specific embodiment, the nucleic acid is DNA, and in particular, a very high molecular weight DNA having greater than about 100 kilobases. In some embodiments the high molecular weight DNA is at least 300 kilobases in length. Methods for isolation of very high molecular weight are known (see. e.g., Murry and Thompson, 1980, *Nucleic Acids Research* 10:4321-5; and Kovacic, R., ET AL., 1995, 23(19) Nuc. ACIDS RES. 23(19) 3999-4000).

According to one method, very high molecular weight DNA is isolated from eukaryotic cells embedded in agarose plugs to minimize shearing. The DNA is separated from other cellular components by PFGE and subsequently electroeluted from the agarose into TE buffer at a concentration in a range of about 0.01 ng/µl to about 0.5 ng/µl. The DNA may be denatured into single stranded form from double stranded form using thermal or chemical denaturation methods known to those of skill in the art. See Barnes, W., 91 PNAS 2216-2220 (1994). For example, thermal denaturation of double stranded DNA may be carried out by heating the DNA sample to 94° C. for 2 minutes. The denaturation step may take place before labeling and may take place before threading the nucleic acid. It is desirable to convert dsDNA into ssDNA prior to labeling, if sequencing is carried out using ssDNA, however, it is not necessary and dsDNA may be labeled as understood by a skilled artisan.

Nucleic Acid Labeling

In step 106, specific bases of the nucleic acid are labeled with contrast agents, such as high-Z atoms, for efficient detection by electron microscopy. The nucleic acid should be associated with electron dense atoms in a manner that is at least partially base specific. A contrast agent or label that is partially base specific (i.e., "base selective") will preferentially associate with one or more of the four DNA or RNA bases over the others (e.g., stains A strongly, G less strongly, T not at all). A contrast agent is completely base specific if it associates essentially with only one base (e.g., A) or sequence (e.g., a particular dimeric sequence). A considerable number of methods for labeling DNA are known and can be used in the invention. For example, base-specific and/or base selective heavy metal staining protocols are described by Whiting ET AL., 474 BIOCHIMICA ET BIOPHYSICA ACTA 334-348 (1977), Jelen ET AL., 10 GEN. PHYSIOL. BIOPHY. 461-473 (1991), and Dale ET AL., 14(11) BIOCHEMISTRY 2447-2457 (1975), all of which are herein expressly incorporated by reference in their entirety. The invention should not be construed to be limited to any particular method of nucleic acid labeling and as appreciated by those skilled in the art, many methods have been described in the scientific literature.

Depending on the method used, each nucleic acid base may be exclusively labeled with a different high-Z labeling compound, selected subsets of nucleic acid bases may be labeled with a different high-Z labeling compounds, or selected subsets of nucleic acid bases may be labeled with the same high-Z labeling compound, such as Os-bipy (as described below). According to one specific embodiment, each DNA base, for instance A, G, C, and T, is exclusively or preferentially labeled with a different Z-labeling compound. A large variety of high-Z labeling compounds may be employed in the methodologies of the invention including, but without limitation, compounds that contain Pt, Hg, I, Rh, Au, Ir, Ag, Os, and the like. Different bases may be distinguished, for example, based on differences in the high-Z labeling agents or between high-Z agents and unlabelled bases, which should be nearly invisible. For example, Os-bipy and iodine can be distinguished based on their scattering cross-sections. Also, for example, a single Au atom bound to all A bases can be distinguished from a three Au cluster bound to all G bases.

Because, in the method of the invention, the TEM imaging detects numerous non-overlapping DNA stands with consistent base spacing, the fidelity of labeling is not critical. Thus, one advantage of the methods of the invention is that the nucleic acid can be labeled chemically and that for a given reaction batch, it is not necessary that all target bases in each strand be labeled (for example, it is not necessary that each T in a strand be labeled when T-specific labeling is used). Complete label accuracy is not necessary because multiple images of the same strand can be combined to determine the underlying sequence because the number of unlabeled bases between the label bases can be determined. For illustration, consider a specific genomic sequence that is represented twenty times in a batch of DNA (i.e., twenty molecules all sharing a region common to that position are present in the batch). For example, the batch may be adjusted to contain about 20 genome equivalents of total DNA. Assume that the base identity of a specific position in the sequence is T, all twenty molecules contain a T at that position. The batch of DNA containing these molecules is subjected to a particular reaction condition known to label any given T between 90% and 100% of the time and to label any given A, C, or G between 0% and 10% of the time. Upon imaging, that position may be seen as labeled in this case in nineteen of the molecules, and unlabeled in one of the molecules. Similarly, an "A" may be labeled in one of the molecules, and unlabeled in nineteen of the molecules. A probabilistic treatment will assign the correct identity to that position in the genome with extreme accuracy. In this case, the identity of the position labeled in 19/20 molecules is "T" and the identity of the position labeled in 1/20 molecules is not T." Furthermore, alignment and joining of sequences can be effected by probabilistic treatments known to those skilled in the art.

Another advantage of the methods of the invention is that sequence information for complementary strands can be derived, which also provides additional statistical support for the validity of a given base determination, i.e., high confidence in the positions of T on one molecule and high confidence in the positions of A on the complementary strand go hand-in-hand. Thus, for example, it is possible to confidently determine positions of all A and T in a sequence from a compound/reaction condition batch that only allows for good discrimination of T in terms of labeling chemistry. The labeled Ts on each strand define A positions on the complementary strand.

Therefore, in some embodiments, only a subset of nucleic acid bases are labeled. For example, aliquots of DNA are separately labeled in a manner that is at least partially base specific. In one approach, a solution containing a plurality of nucleic acid molecules is reacted under conditions that label at least about 70%, sometimes at least about 80% and sometimes at least about 90% to about 100% of one or more specific nucleotide bases (A, T, G or C) and less than 20, preferably less than 10% of at least one nucleotide base. For example, the solution is reacted under conditions where about 90% to about 100% of T and C are labeled while labelling a small percentage of A and G.

In one embodiment, the DNA aliquots may be labeled with Os-bipy using different conditions in order to achieve different base-specific labelling densities. See Example 1, infra. In this approach, the DNA of interest is isolated and divided into two solutions, i.e., solutions 1 and 2 at a concentration in a range of about 0.01 ng/µl to about 1 ng/µl in each solution. Each solution is reacted with Os-bipy using different conditions (as described in further detailed below) in order to achieve different base-specific labelling densities. Furthermore, selected solutions are subjected to a pre-treatment prior to reacting with Os-bipy, such as a bisulfite pre-treatment, as described below and in Example 1, infra.

Solution 1 is reacted for 20 hours at 26° C. with a four-fold molar excess of Osmium tetroxide and of 2,2'-bipyridine in TE buffer pH 8.0 with 100 mM Tris and 10 mM EDTA; these conditions label about 100% of T's, about 85% of C's, about 7% of G's, and about 0% of A's. Solution 2 is reacted under the same conditions as Solution 1 except that the reaction only proceeds for 15 minutes, and only a 2.5-fold molar excess of Osmium tetroxide and of Os-bipy is used; these conditions label about 90% of T's, about 8% of C's, about 5% of G's, and about 0% of A's. As described below, using the methods of the invention, it is possible to compare these results to those obtained for a short incubation time reaction, and thereby determine the base-specific pattern for C, and by extension for G on the complementary strand. By extension, it is also possible using the methods of the invention to determine the base-specific pattern for T and by extension for A on the complementary strand. Thus, a single labeling compound with two reaction conditions can be used for determination of the pattern of T, A, G, and C.

It is also to be appreciated that the invention allows for determination of patterns of cytosine methylation using Os-bipy. In this case four aliquots (solutions 1, 2, 3 and 4) are used. Solutions 1 and 2 are treated as was Solution 1, above. Solutions 3 and 4 are treated as was Solution 2, above. However, prior to Os-bipy reactions, Solutions 2 and 4 are first subjected to a bisulfite treatment to convert unmethylated C residues to U. This allows the pattern of methylation to be determined by comparing sequences from solutions treated with bisulfite to those left untreated. See Jelen ET AL. 10 Gen. PHYSIO. AND BIOPHYS 461-473 (1991). Both methylcytosine and U have labeling efficiencies under different conditions in the reaction with Os-bipy that are distinguishable from labeling efficiencies for the canonical four bases. Thus, in order to derive epigenetic modification information for a genomic sample, it is possible either to determine the base-specific pattern of methylcytosine in the context of DNA that has not been treated with bisulfite or the pattern of U in the context of sequencing after bisulfite treatment. After the labeling reaction, unlabeled osmium is removed by ultrafiltration or dialysis to minimize extraneous heavy atom contamination during the imaging process and the DNA polymers are diluted to about 0.1 ng/µl in TE buffer pH 8.

Many other high atom base-specific high atom labeling methods are known to those skilled in the art. Some examples are as follow: Beer and Moudrianakis described the use of a diazonium salt compound coupled to uranyl ions for the labeling of guanine residues (Beer, M. and Moudrianakis, E., *Determination of Base Sequence in Nucleic Acids with the Electron Microscope* 48(3) PNAS, 409-416 (1962)). Robert Whiting used Pt-DMSO [Platinum Dimethylsulfoxide, KPtCl3(DMSO)] to achieve differential labeling suitable for the identification of adenine nucleotides (Studies of Nucleic Acid Sequences by Dark Field Electron Microscopy, Ph.D. Thesis, (1975), University of Toronto, School of Graduate Studies). Mecuration of cytosine residues using mercuric acetate was reported by Dale and coworkers (Direct covalent mercuration of nucleotides and polynucleotides, Dale, RMK, ET AL., 14 BIOCHEMISTRY, 2447-2457 (1975)). Another approach to labeling DNA is first to modify it covalently in a base-specific manner so that it accepts heavy metal labels at the modified bases. One example of this approach was described by Seth Rose, who modified adenine and cytosine residues with chloroacetylaldehyde so that mercuric acetate or osmium tetroxide could subsequently bind these residues (Rose, S D., *Mercuration of Modified Nucleotides: Chemical Methods Toward Nucleic Acid Sequencing by Electron Microscopy*, 361 BIOCHIM. BIOPHYS. ACT., 231-235 (1974)).

In a further embodiment, cluster labeling may be employed in the methods of the invention. Cluster labels are label compounds that contain more than a single heavy atom. Cluster labels may be used in protocols that utilize stretching methods that provide sufficient base to base separation. Sufficient separation is necessary in order to obtain sequence data that is not limited by steric hindrance between neighboring attached clusters. Clusters can be attached to oligomers and then the oligomers are hybridized to DNA through complementary base pairing. In this manner, complementary sequences could be localized using electron microscopy. In order to efficiently achieve full sequence data, information can be combined from imaging of separate batches of very short cluster-labeled oligomers (trimers and tetramers) hybridized to unknown sequences. In particular, the very short cluster-labeled oligomers may have a length in a range of about 5 to about 20 bases. Clusters that can directly label unmodified DNA, i.e., DNA that has the natural composition of bases without unnatural bases containing functional groups that may increase the efficiency of cluster labeling, include the triosmium compound as described in Rosenberg ET AL., 689 J. ORGANOMETAL. CHEM. 4729-4738 (2004). Cluster labeling of DNA strands in which specific modified nucleotides have functional groups such as aminoallyl or thiol groups that would allow efficient reaction with commercially available cluster label reagents such as monomaleimido undecagold from Nanoprobes Inc. (Yaphank, N.Y.). Commercially available cluster labeling reagents that can be functionalized with linkers that react with DNA in a base-specific or base selective manner include triosmium dodecacarbonyl, triruthenium dodecacarbonyl, and tetrairidium dodecacarbonyl (all three available from Sigma Aldrich Corp., St. Louis, Mo.) and monomaleimido undecagold (Nanoprobes, supra). Cluster labeling with sterically hindered clusters can be made more efficient by performing the labeling reactions on DNA that is stretched in solution. Labeling may also be performed inside a fine tube (about 30 nm to about 1 μm in diameter) where the DNA is elongated within the tube or capillary with known techniques (Chan, E., and Goncalves, N., 14(6) GENOME RES. 1137-1146 (2004)), in solution, and reacts with a label. This method has the advantage of preventing cross-linking from labels that have more than one binding site (e.g., Nanogold).

In one embodiment, cluster labels may be employed as contrast agents, known clusters may be attached to nucleic acid polymers in a base-specific or base-selective manner using chemical linkage structures known to bind or modify nucleic acid polymers base-selectively or base-specifically. This approach to cluster labeling may be referred to as "piggybacking." Piggybacking may be carried out in the following manner, for example. Mercuric acetate may be used to mecurate cytosine, as described in Dale, R., ET AL., 14 BIOCHEMISTRY 2447-2457 (1975), and a cluster compound that will attach to cytosine may be prepared with a mercuric acetate moiety by acetylating the mercury-bridged triosmium cluster (mu3-eta2-c2-t-Bu)Os3(CO)9(mu-Hg)I, which is described in Rosenberg, E., ET AL., 10 ORGANOMETALLICS 203-210(1991). As another example of piggybacking, phenanthroline is known to form a complex with osmium tetroxide which can be used as a base-selective label. (Paecek, E., ET AL., J. 13(3) BIOMOL. STRUCT. DYN. 537-46 (1995)). 5-amino phenanthroline (polysciences, Inc., Warrington Pa.) can be attached via its exocyclic amine group to the succinimdyl ester of diphenylphosphino propionic acid (Argus Chemicals SRL, Vernio, Italy). The phosphine can be ligated to any of several cluster compounds by techniques known to those skilled in the art (Cheng ET AL., 127 J. STRUCT. BIO. 169-76 (1999). As still another example of piggybacking, cluster compounds can be derivatized with alkylating moieties, such as sulfonate esters. Relevant synthetic procedures are described in Susan Ermer, ET AL, J. ORGANOMET. CHEM., (1980), 187, 81-90. The use of sulfonate esters to alkylate nucleic acid polymers is described in Yi-Zhang ET AL., 32(31) BIOCHEMISTRY 7954-7965 (1993).

The invention provides methods for obtaining sequence information of a nucleic acid polymer by determining the positional sequence of selected bases in a specified region of a nucleic acid (e.g., DNA) strand. By sequence information is meant that the position of one or more nucleic acid bases of both labeled and unlabeled bases are known and by positional sequence is meant that the positions of at least one base (e.g., T) relative to other bases is determined. For example, in a 25 base DNA strand in which Ts are labeled, the positional sequence within a 25 base region may be described as follows:

T000T0000TTT00T00T000T00T where "0" is a base other than T. Thus, detecting the position of Ts and non-Ts allows one to determine the positional sequence of Ts. As will be understood from this description, the positional sequences of T and/or C and/or G and/or A or combinations thereof can be determined. The method of the invention provides a method for determining the positional sequence of at least one base in a single nucleic acid strand with at least 70% accuracy, alternatively at least 80% accuracy, and often at least 90% accuracy. The positional sequence may be determined in a region comprising at least 100 up to one million bases, sometimes 200 to one million bases, sometimes 1000 to one million bases, sometimes 10,000 to one million bases. In some embodiments the positional sequence is determined in a region of at least 200, at least 1000, at least 5000, at least 10,000, at least 100,000 or at least one million bases of a strand. In one embodiment the positional sequence of at least one base is determined for a region comprising 1000 to 100,000 bases. The accuracy of the method may be determined by re-sequencing DNA of known sequence.

"Positional sequence" is one type of sequence information. It will be apparent from this disclosure that by comparing positional sequence for individual bases (or combinations of bases) it is possible to obtain more complete sequence information, including the positional sequence of all four bases (i.e., complete sequence) within a region of the strand or genome.

Advantageously, the sequencing method(s) of the invention do not rely on incorporating modified nucleotides into DNA or a nucleic acid strand. Although the method is compatible with, and may be used with, enzymatically incorporated labels (e.g., incorporated during polymerization) it is more often used with naturally occurring DNA strands that isolated and labeled directly (using, for example, labels described above and in the literature). Moreover, the present method allows (but does not require) sequence to be determined for a single stranded DNA rather than a double stranded molecule, thus eliminating ambiguities that may arise with other approaches.

Nucleic Acid Suspension

In Step 108, individual nucleic acid polymers are stretched into empty to space to ensure consistent base to base spacing within the nucleic acid strand. According to one embodiment, individual DNA strands are extended into space (i.e., a substantial portion of the length of the strand is not supported by a substrate or suspended in a solution or buffer). The suspended DNA essentially free from solution or buffer can then be transferred to an imaging substrate for imaging. This process may be referred to as DNA threading, discussed in detail below.

Suspension of DNA out into empty space results in consistent base-to-base spacing of the nucleic acid polymer. Conceptually this is analogous to grabbing both ends of a spring with two hands and stretching, such that each loop of the spring is the same distance from the next loop because they all experience the same amount of force. This causes the heavy atom labels that are seen in the electron microscope to be spaced in a manner corresponding to their actual spacing along the nucleic acid polymer and to the spacing of the specific bases to which they are attached. Moreover, the positions of unlabeled bases can be determined based on the consistent spacing.

In a specific embodiment, the DNA is suspended using a tool to which an end of a DNA strand is attached. The tool may be dipped into a solution (typically a droplette) containing a plurality of nucleic acid polymer strands or a single strand, a nucleic acid strand may preferentially bind to the tip of the tool, and as the tool is pulled out of solution, the nucleic acid molecule is suspended in space such that a first end of the nucleic acid strand is in the solution, a second end of the nucleic acid is attached to the tool, and a region between the ends ("suspended region") is suspended in space. It will be understood that the "end" of the DNA molecule is not necessarily defined by the physical termini of the molecule in solution (e.g., 5' phosphate and 3' hydroxyl groups). For example, a 140 kb molecule might have 20 kb at one end in the droplet, 100 kb in the suspended region and 20 kb at the other end bound to the needle. The nucleic acid strand is suspended such that the bases of the nucleic acid polymer strand are extended such that there is consistent base-to-base spacing of the bases. Specifically, the base-to-base spacing or periodicity is in a range of about 3 Å to about 7 Å between the bases, which may be measured from center to center of each phosphate.

In one embodiment, the droplette may have a volume in a range of about 0.5 µl to about 50 µl, sometimes a volume in a range of about 1 µl to about 25 µl, sometimes a volume in a range of about 1 µl to about 15 µl, sometime a volume a volume in a range of about 1 µl to about 10 µl, and sometimes a volume in a range of about 1 µl to about 5 µl.

In one embodiment, at least a portion of the single nucleic acid polymer strand may be suspended in space between the tool and the liquid. The bases of the nucleic acid polymer strand may be extended such that there is consistent base-to-base spacing of the bases. The base-to-base spacing may be in a range of 3 Å to about 7 Å between the bases, and specifically about 5 Å. The nucleic acid polymer strand may be extended such that the strands are linear.

The tool used to extract the DNA molecule into empty space (e.g., out of a droplette) may be any of a variety of devices so long as it can be used to bind a single nucleic acid strand and suspend it into space. In some embodiments, the tool is a sharp needle, a hollow needle, or small (i.e., less than about 300 nm in diameter) magnetic particle that has an affinity to bind nucleic acids used with a magnetic probe.

Figure 2:
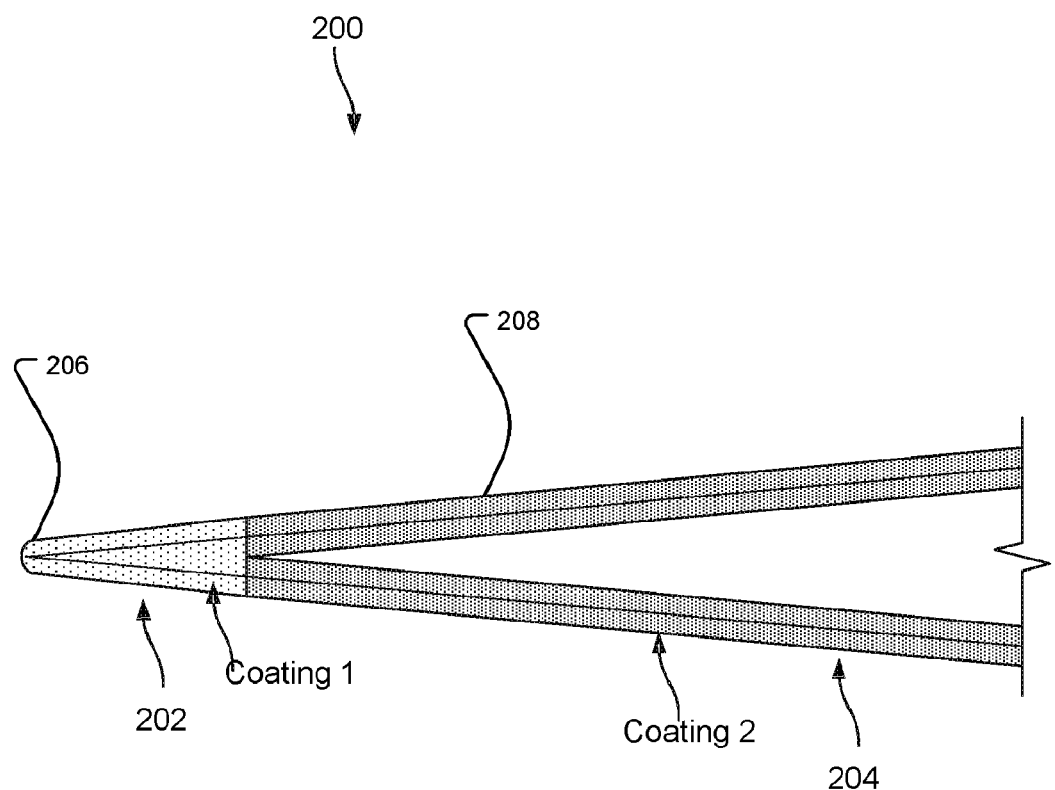
FIG. 2 is schematic showing a needle functionalize with coating 1, which is capable of binding to a nucleic acid strand and coating 2 which does not bind to a nucleic acid strand.
Figure 3:
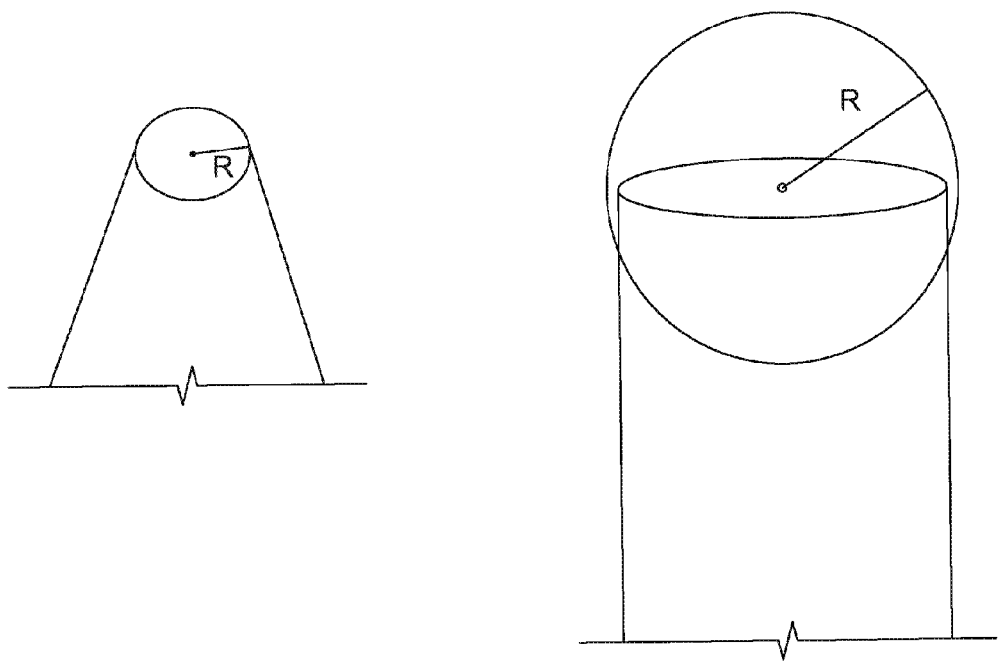
FIG. 3 shows a schematic of the radius of curvature of the sharp needle.

In one approach the tool is a sharp needle. The sharp needle may be composed of materials such as glass, gold, tungsten, PMMA, polystyrene, PVC, silicon, or any other suitable substance that may be made into a very sharp needle. The needle tip can be readily made by techniques known to those of ordinary skill in the art, such as using a standard pipette puller, microfabrication (Handbook of Microlithography, Micromachining & Microfabrication, P. Rai-Choudhury, SPIE Optical Engineering Press, 1997), growth, or molding and casting. For example, a glass needle can be made by heating the middle of a glass fiber (about the same diameter as a microcapillary tube) in an ethanol flame and pulling from either end of the fiber. Alternatively, a standard pipette puller can be used. In one embodiment, as shown in FIG. 2, the needle 200 may have a proximal end 202 including a tip 206 having a diameter less than about 200 nm, a distal end 204, and a shaft 208 extending between the proximal end and distal end. The tip 206 may have a diameter less than, up to about or greater than about 1 µm. The tip diameter can be determined using SEM. The terminal radius of curvature would be measured in a geometrically consistent manner, e.g., one would identify a rounded area at the tip and would interpose an imaginary circle fitted to the curvature, and one would then measure the radius of that circle by measuring the distance from its center to its periphery. In some cases the rounded arc at the end of the needle will only roughly approximate the outer edge of a circle (FIG. 3). In other cases the end of the needle is broken to resemble a flat mesa about 20 nm to about 500 nm across. A preferred diameter may be less than about 300 nm.

The tip of the needle may be functionalized by coating with a material that preferentially binds to the end of a nucleic acid, and may include without limitation, PMMA, polystyrene, PVB, chemical treatments such as silanization, oligo- or polynucleotides complementary to genomic sequences or restriction site overhangs (the oligomers may possess degenerately pairing bases such as inosine, allowing for greater selective range), aptamers with high affinity to specific sequences or structures, streptavidin or other proteins with a high affinity to a molecule such a biotin, or any other suitable material that would specifically attach to the ends of the nucleic acid. In one specific embodiment, the needle tip may be coated with PMMA by dipping in about 0.5% PMMA solution in acetone, and drying in an acetone saturated atmosphere.

In a further embodiment, the tip of the needle may be coated with a second coating, to limit the area where the nucleic acid can bind, and may include materials such as octanethiol, nonanethiol, hexadecanethiol, or other linear alkane-thiol chains. In FIG. 2, coating 1 binds to the ends of the DNA, while coating 2 does not bind or binds less avidly. For example, in one approach, a gold needle tip may be dipped into a solution of polystyrene, and then the polystyrene may be crosslinked just at the very tip in an electron beam. Subsequently, the un-crosslinked polystyrene may be removed from the rest of the needle by methods known to those skilled in the art such as dipping in acetone or chloroform. The needle could then be dipped into an octanethiol solution, which will form monolayers on gold but not on the polystyrene. The ends of the DNA will not bind to the octanethiol region.

In another embodiment, magnetic nanoparticle oligonucleotides may be used to specifically label the ends of the nucleic acid polymer strands. In this approach a tool having a magnetized end is dipped into the solution containing the magnetic labeled nucleic acid polymer strands and binds to the end of a single molecule of the nanoparticle labeled nucleic acid polymer strand. As the magnetized tool is pulled out of the solution, the nucleic acid molecule is extended and suspended in space such that a first end in of the nucleic acid strand in is the solution and a second end of the nucleic acid is attached to the tool. The nucleic acid strand is suspended such that the bases of the nucleic acid polymer strand are extended such that there is consistent base-to-base spacing of the bases, and specifically, the base-to-base spacing is in a range of about 3 Å to about 7 Å between the bases, and in particular 5 Å.

In one embodiment, the sharp tool may be a hollow needle. In particular, hollow micro-needles may be manufactured with techniques known in the art, so that a nucleic acid solution may be pumped through the bore. Subsequently, the micro-needles may be touched to either a support substrate with an affinity for nucleic acid ends or to a sharper polymer-coated solid needle in order to thread directly out of the hollow bore. Thus, the hollow micro-needles could serve as both direct threading implements and as channels for precise solution control. The bore may be fabricated by techniques known in the art that only one strand would enter the bore-length-wise, and assist in controlling nucleic acid thread concentration. This is technique using a hollow needle is consistent with pulling DNA out of solution using a sharp tool. The difference with using the hollow needle is that the surface and shape of the solution happens to be very small and constrained by the walls of the hollow needle.

Figure 4:
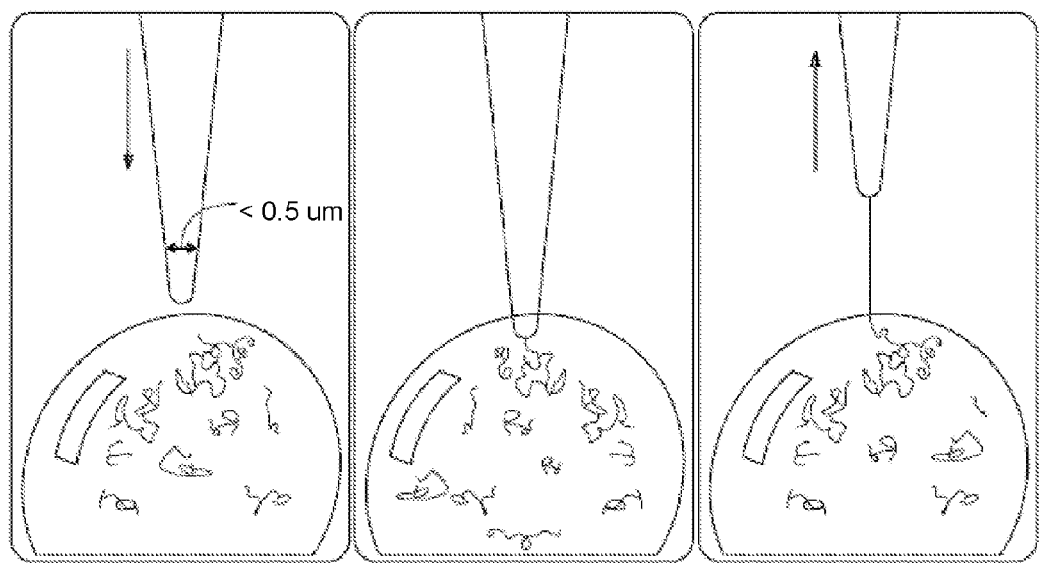
FIG. 4 is a schematic illustration showing a method according to principles of the invention for extending a nucleic acid strand into empty space. Panel I shows a tip of the needle and a droplet of solution containing a plurality of nucleic acid strands. Panel II show the tip of the needle moving into the droplet of solution containing the nucleic acid strands and binding to a single nucleic acid strand. Panel III shows the nucleic acid strand being stretched out into empty space.

After the sharp needle is functionalized, the nucleic acid is "threaded" or attached onto the sharp needle. In one embodiment, DNA threading is performed by dipping the sharp functionalized needle into and out of the DNA polymer solution, pulling the DNA strands into empty space as shown in FIG. 4. The needle tip may be moved into and out of solution at a rate in a range of about 1 nm/hr to about 10 m/s, and specifically, at a rate in the range of 1 µm/s to about 10 mm/s. It is appreciated that the DNA strands pulled out remain normal to the surface of the DNA solution. Nanopositioners including piezo-actuators, such as those used in AFM, may be used to control the position and motion of the needle with sub-angstrom precision (using high quality feedback mechanisms). Nanopositioners are known in the art and are described, for example, in U.S. Pat. No. 5,903,085 and are commercially available from Piezosystem Jena (Germany). Variables that affect efficient threading of single strands include solution temperature and pH, humidity of surrounding atmosphere, the concentration of labeled ssDNA in solution, the speed the needle is dipped into and out of the solution, the length of time the needle sits in solution, the sharpness of the needle and coating, and the depth and angle of entry as the needle is dipped into solution.

Figure 5:
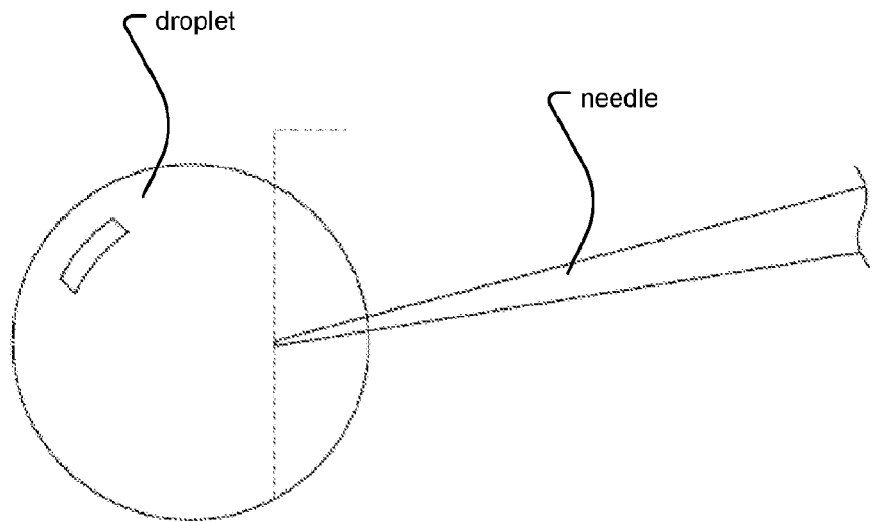
FIG. 5 is a schematic showing the maximum dipping depth of the needle tip into the droplet of solution containing the nucleic acid strands (Panel I) and the minimum dipping depth (Panel II).
Figure 5:
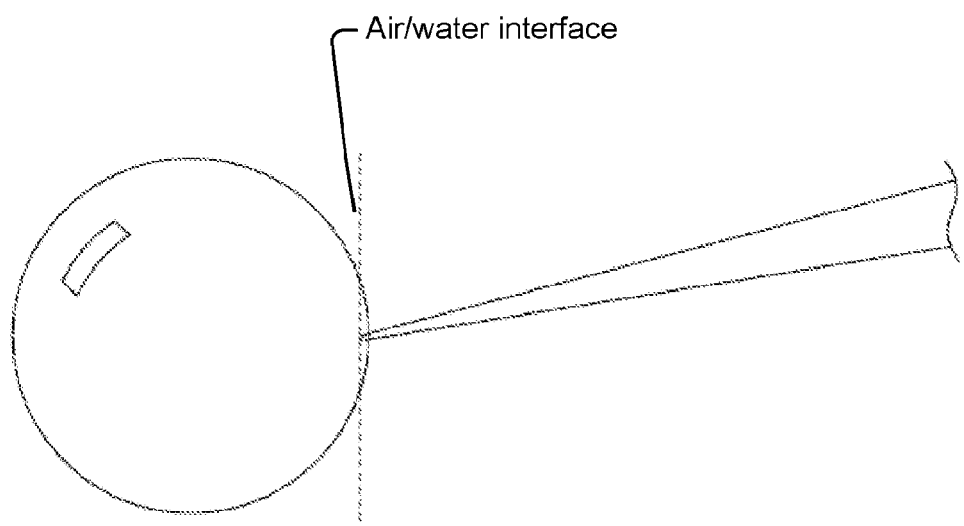
Figure 6:
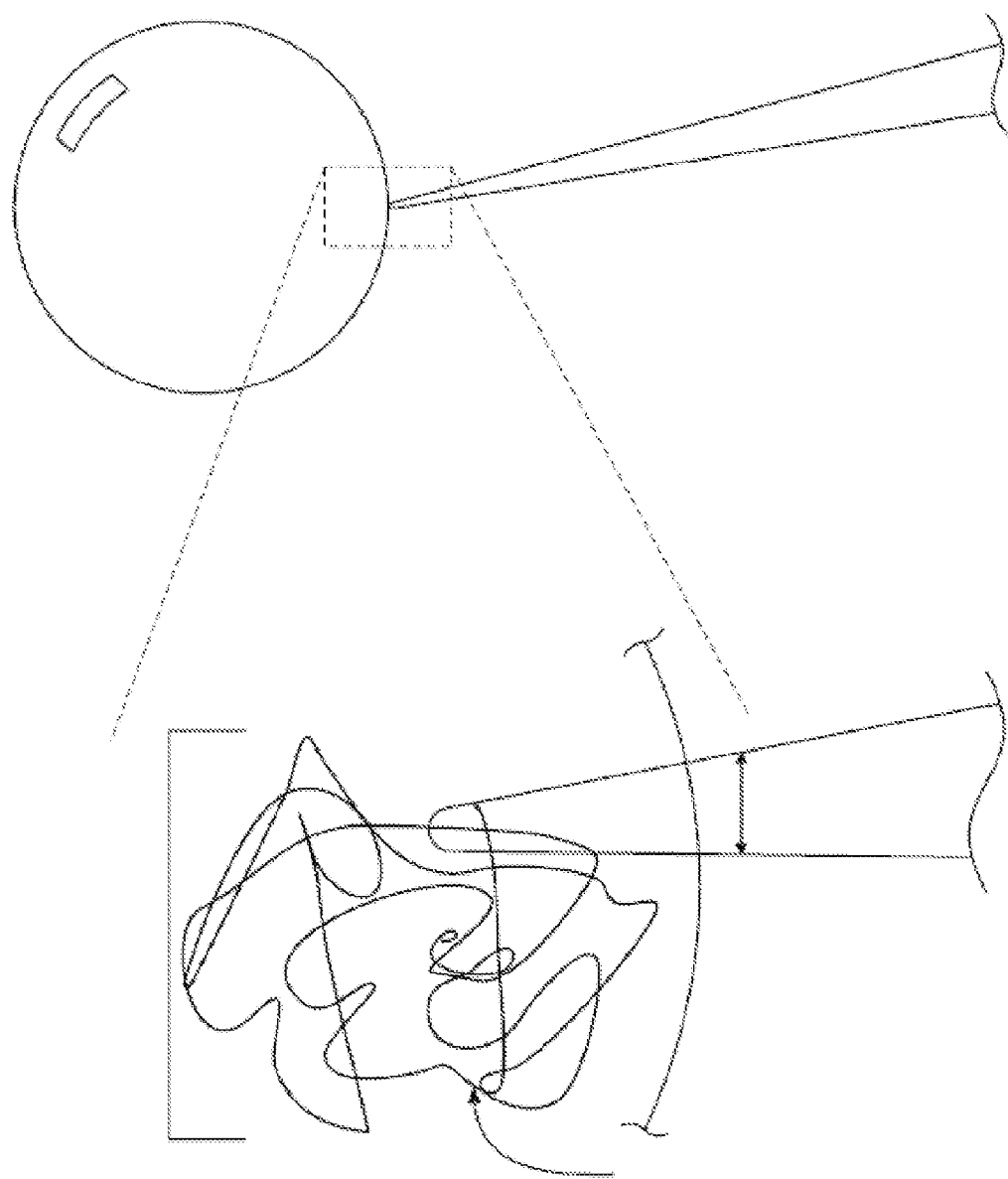
FIG. 6 is a schematic showing the minimum dipping depth of the needle tip into the droplet of solution containing nucleic acid strands. The expanded view schematically shows a needle tip in a droplet of solution specifically binding to a single nucleic acid strand, which may be in solution or at the atmosphere/solution interface.

The "dipping in" distance is a variable that may control the amount of DNA that attaches to the needle (FIG. 5). For example, for high molecular weight DNA having a concentration in a range of about 0.01 ng/μl to about 0.5 ng/μl, the needle dipping may be a depth in a range of about 1 Å to about 20 μm into the solution. In one embodiment, shallow dipping is used (FIG. 6). With shallow dipping, the needle is placed into the solution in a very short distance (for example, less than about 1 μm) amount to limit the surface area of the needle available for strand binding. Multiple needles and/or an automated system can be used for threading the needle.

Another variable is the amount of time the needle stays in solution. The number of nucleic acid molecules that attach to the tip may be regulated by controlling the amount of time the tip is allowed to remain in solution. For a given solution, longer needle dwell times will result in more attachments, and shorter times will result in fewer attachments, as a function of the time required for a molecule to diffuse in solution and attach to the needle. This time range can vary from less than about 1 ns, to multiple seconds or minutes.

For example, a large number of ultra-sharp needles could be placed on a single nanopositioner-driven support with close spacing so that a single dipping motion could pull a large number of strands simultaneously, with enough separation to avoid interference between strands. A parallel or "bed" of needles could also be made by microfabrication techniques known by those of skill in the art.

Once the nucleic acid is attached onto the needle, the needle is pulled out of the solution, and thus the nucleic acid bases are extended out into empty space to ensure consistent spacing between the bases. The extended nucleic acid should have a base-to base spacing in a range of about 3 Å to about 7 Å, and specifically about 5 Å. The spacing of the bases, however, should not be construed to be limited exclusively to this range, as the appropriate spacing of bases will depend on a number of factors, such as whether the nucleic acid is stretched further by use of a shelf (described below). The forces acting between the air-water interface and the needle tip alone should lead to a base-to base spacing of about 5 Å or a force of about 65 pN. The total length of a particular extended strand in empty space will correspond to the number of bases in the strand times the average base-to-base spacing. For example, a strand about 10 million bases long may be stretched to a length of about 5 mm given a 5 Å base-to-base spacing. The nucleic acid strand may be stretched to a length of about 20 nm, sometimes to a length of about 100 nm, sometimes to a length of about 200 nm, and sometimes to a length of about 1 μm. It should be noted, that the distribution of lengths in a particular pool of nucleic acid may have to be taken into consideration. This is so that strands are not completely pulled out of solution so that meniscus forces at the air-solution interface can continue to apply tension at the end of a strand distal to the needle tip. With a solution containing a longer length nucleic acid polymers, the nucleic acid strands will be pulled greater distances from the solution relative to a solution containing shorter length nucleic acid polymers. Sufficient extension to get consistent base-to-base spacing is a linear function of the molecular weight of the nucleic acid molecules. In specific embodiments, the nucleic acid strand may be stretched and extended to a length of at least about 2 μm, more specifically, to a length of at least about 25 μm, even more specifically to a length of at least about 50 μm, and more specifically yet, to a length of at least about 100 μm.

Since the forces involved in stretching the nucleic acid do not break covalent bonds, the nucleic acid will not break during the stretching process. The meniscus forces acting at the air-water interface are strong enough to remove the secondary structure, but not strong enough to break the covalent bonds. If the threading device is arranged and programmed such that additional force is applied beyond that required to pull the DNA out of solution care must be taken not to break the DNA.

Figure 21:
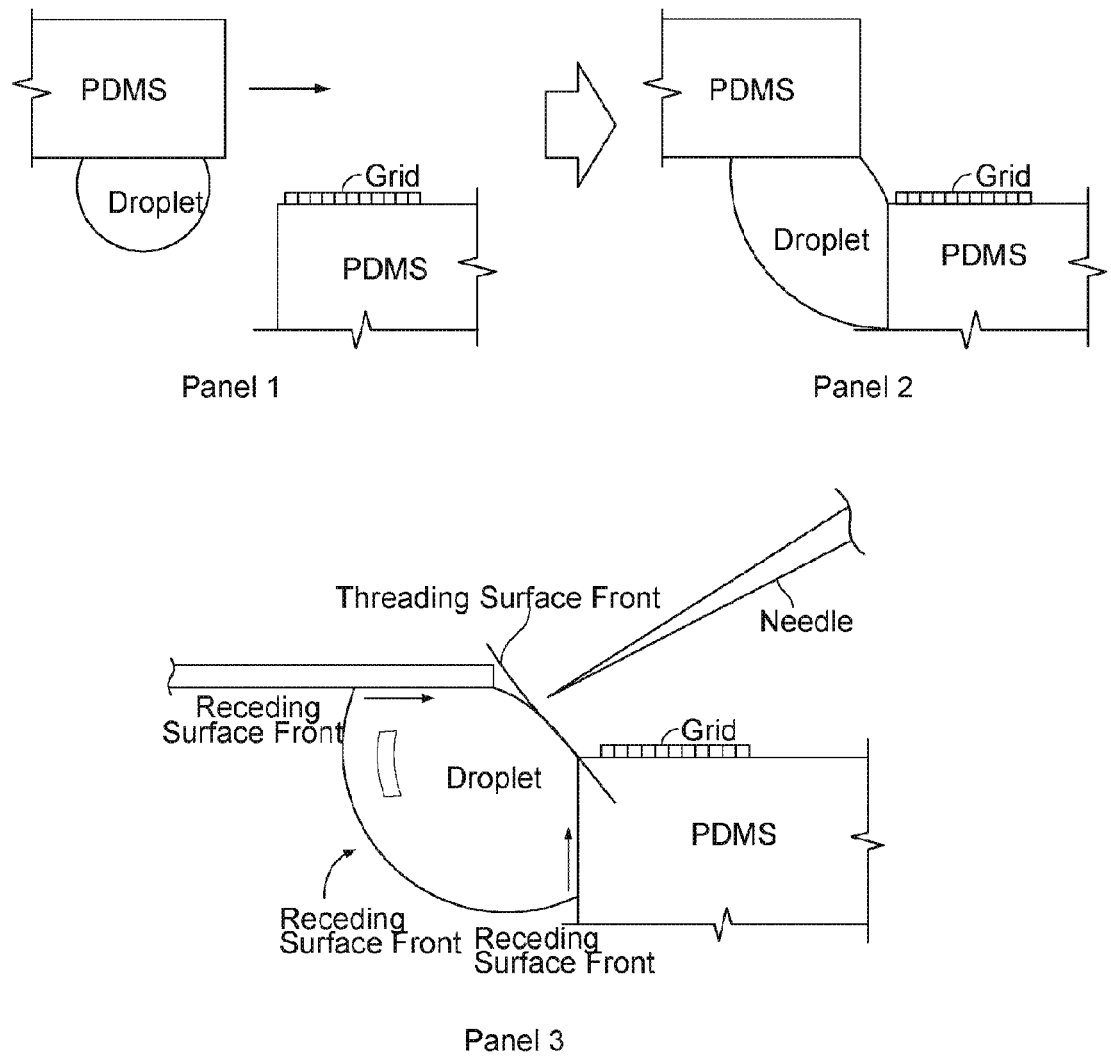
FIG. 21 is a illustration showing a simple mode droplet holder.

It is desirable to minimize evaporation and/or control the position and angle of the droplet in many embodiments. In the simplest mode, the droplet is held stationary with the careful positioning and configuration of a PDMS holder piece. In FIG. 21, panel I shows the approach of a droplet to the grid holder piece. Panel II shows the droplet held between two pieces of PDMS such that the droplet will maintain the threading surface front. Even as the droplet evaporates the threading surface front will stayed unchanged, while only the receding surface front moves Panel III. In another simple mode, a humid chamber is constructed around the threading apparatus such that a state of high (e.g., approaching 100%) humidity is achieved and the droplet will not evaporate.

Alternatively, the nucleic acid strand may be removed from solution and suspended between two points by attaching the nucleic acid strand to two points in solution using optical or magnetic beads (Bustamante, C., ET AL., 421(6921) NATURE 423-427 (2003)). The strand is then freeze dried and the ice is then sublimed away, leaving a suspended single strand that can then be transferred to an imaging substrate. In an other embodiment, individual nucleic acid strands are bound to a single magnetic particle, which is then withdrawn from the droplette (e.g., using a magnetic probe) to extend the DNA strand into space.

Attachment to Imaging Substrate

In step 110, once the nucleic acid strands are threaded between the needle and the droplet in empty space and the nucleic acid strand is not surrounded by either solution or buffer, the strands can be placed directly onto a substrate, such as a support substrate or an imaging substrate for imaging by electron microscopy. One approach for doing this is referred to as "shelf threading," in which extended DNA strand are placed on an imaging substrate or are placed on a support substrate and transferred to an imaging substrate in a separate step. See FIG. 7. A related approach is referred to as "gap threading" in which DNA strands are suspended across a gap in a support substrate and transferred to an imaging substrate in a separate step. See FIG. 15.

The strands can be placed in a great many orientations including orientations in two and three dimensions so long as strands do not overlap or cross in the "suspended region" (or do so rarely). The most convenient and standard method for EM sample preparation is two dimensional, typically with a number of strands positioned parallel to each other. See, e.g., FIG. 8. In this configuration, the ratio of sample to empty or 'non-sample' space can be readily maximized. In general, the closer the interstrand spacing the better, as long as the strands are not in such close proximity that they interfere with the visibility and identification of their neighbors. Sub-nanometer precision positioners are commercially available, and a very convenient configuration is to place the strands in parallel lines ranging from about 2 nm to about 10 nm apart. In another embodiment the strands are positioned radially.

Figure 12:
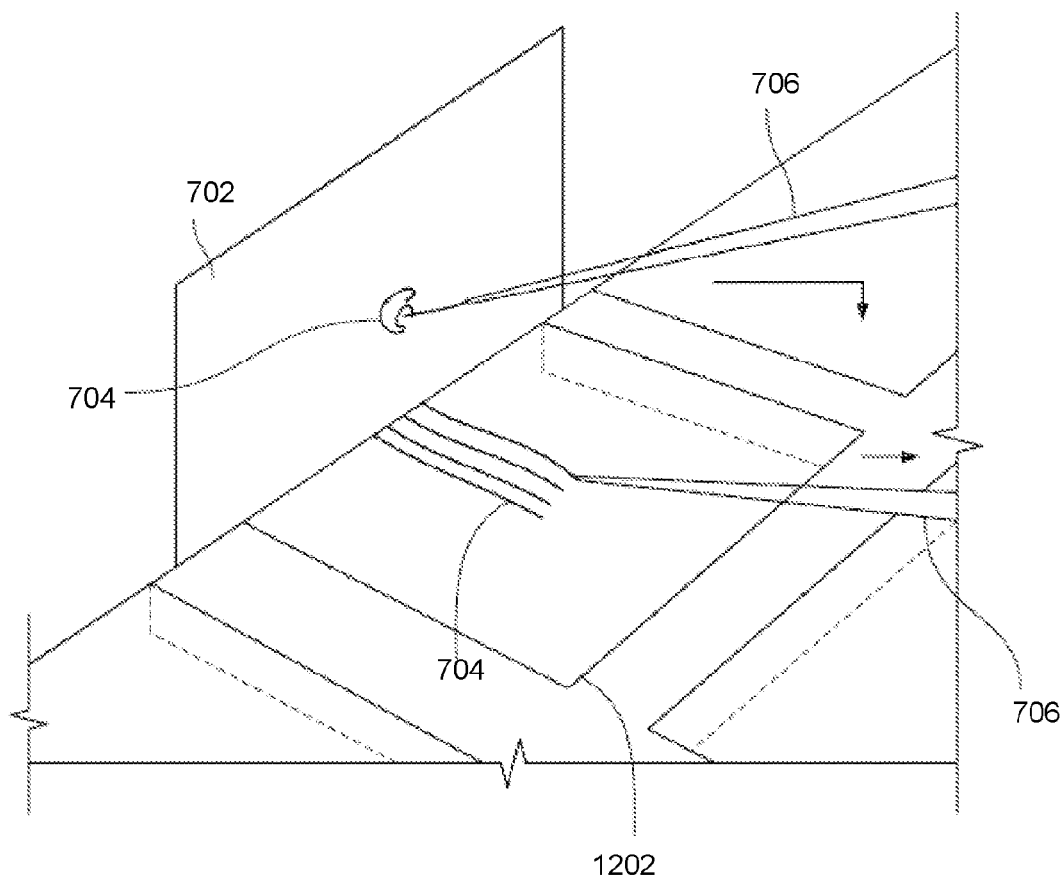
FIG. 12 is a schematic showing large parallel arrays of closely spaced nucleic acid strands, such as DNA strands, that can be formed by repeating the basic programmed piezo-actuator-controlled needle motion order of dipping-in, dipping-out, setting-down, dragging, lifting-up, and translating. The nucleic acid strands in this figure are not depicted as straight as the strands would be in actual practice.

In one embodiment, multiple suspended strands may be placed in a substantially linear orientation. FIG. 12, shows placement of nucleic acid strands 704, such as DNA on a substrate 1202 by needle 706 from a droplet of solution 702 containing nucleic acid strands 704. Large parallel arrays of closely spaced nucleic acid strands, such as DNA strands, can be formed by repeating the basic programmed nanopositioner-controlled needle motion order of dipping-in, dipping-out, setting-down, and optionally dragging the needle tip along the support substrate in order to deposit the strand, lifting-up, and translating over a desired distance between strands. In an industrial, high-throughput scale, millions of strands may be placed onto one support substrate in this manner, particularly using a large array of parallel needles.

Because the method provides DNA strands that are straighter (more linear) than other methods, crowded arrays may be used and accurate sequence determined. Arrays may contain from about 2 to 10 million substantially linear strands and/or parallel strands with a suspension region of length in a range of about 1 µm to about 5 mm and spacing in a range of about 1 nm to about 10 nm, resulting in a density in a range of about 1 base/nm$^2$ to about 1 base/5 nm$^2$. Arrays may have, for example, more than 5, more than 10, more than 100, more than 1000, or more than 10,000 DNA strands.

Notably, the methods of the invention can produce linear (straight) double stranded and single stranded nucleic acid strands. Linearity can be described in terms of dimensions of an imaginary box that encloses the strand (or linear portion thereof) or more conveniently an imaginary rectangle that encloses a two dimensional projection of the strand (or the strand itself) on a supporting substrate. The linear portion of the strand is usually at least about 2 µm in length, more often at least about 5 µm in length, and even more often at least about 10, 20, 30, 50 or 100 µm in length. In some cases the linear portion of a strand will be nearly the entire length of the strand. In one embodiment, the rectangle is such that if the smallest possible imaginary rectangle were drawn to enclose the strand or linear portion such that all portions of were inside the rectangle, the rectangle would have a length to width ratio of not less than 100:1, or preferably at least 160:1, or preferably at least 200:1, more preferably at least 500:1, and even more preferably at least 2000:1. For example, for a linear portion 5 µm in length, a box drawn to enclose a linear threaded strand on a flat surface would be about 30 nm in width (1:160 ratio) or 2.5 nm in width (2000:1 ratio). For a strand that is 10 um long, the bounding box could be 10 µm by 62.5 nm making the ratio 160:1. For a linear portion that is 3 um long, the bounding box could be 4 nm making a ratio of 500:1. In three dimensions the third (depth) dimension of the box would be within a factor of 5 the dimension of the width, preferably within a factor of 2, and most preferably about the same as the width. Because the strands positioned using the methods of the invention are straight (usually along substantially the entire length of the suspended region) neighboring strands in an array may be placed very close together, such as about 2 nm apart, about 3 nm apart, about 4 nm apart, about 10 nm apart, about 20 nm apart, or about 50 nm apart from the other neighboring strands. In some embodiments a plurality of neighboring strands are less than 50 mn apart, preferably less than 20 nm apart, more preferably less than 10 nm apart, or less than 4 nm apart (e.g., 2-50 nm apart, 2-20 nm apart, 2-10 nm apart, 4-50 nm apart, 4-20 nm apart, or 4-10 nm apart). In a specific embodiment, the linear strands are placed such that they do not cross.

Shelf Threading

Figure 7:
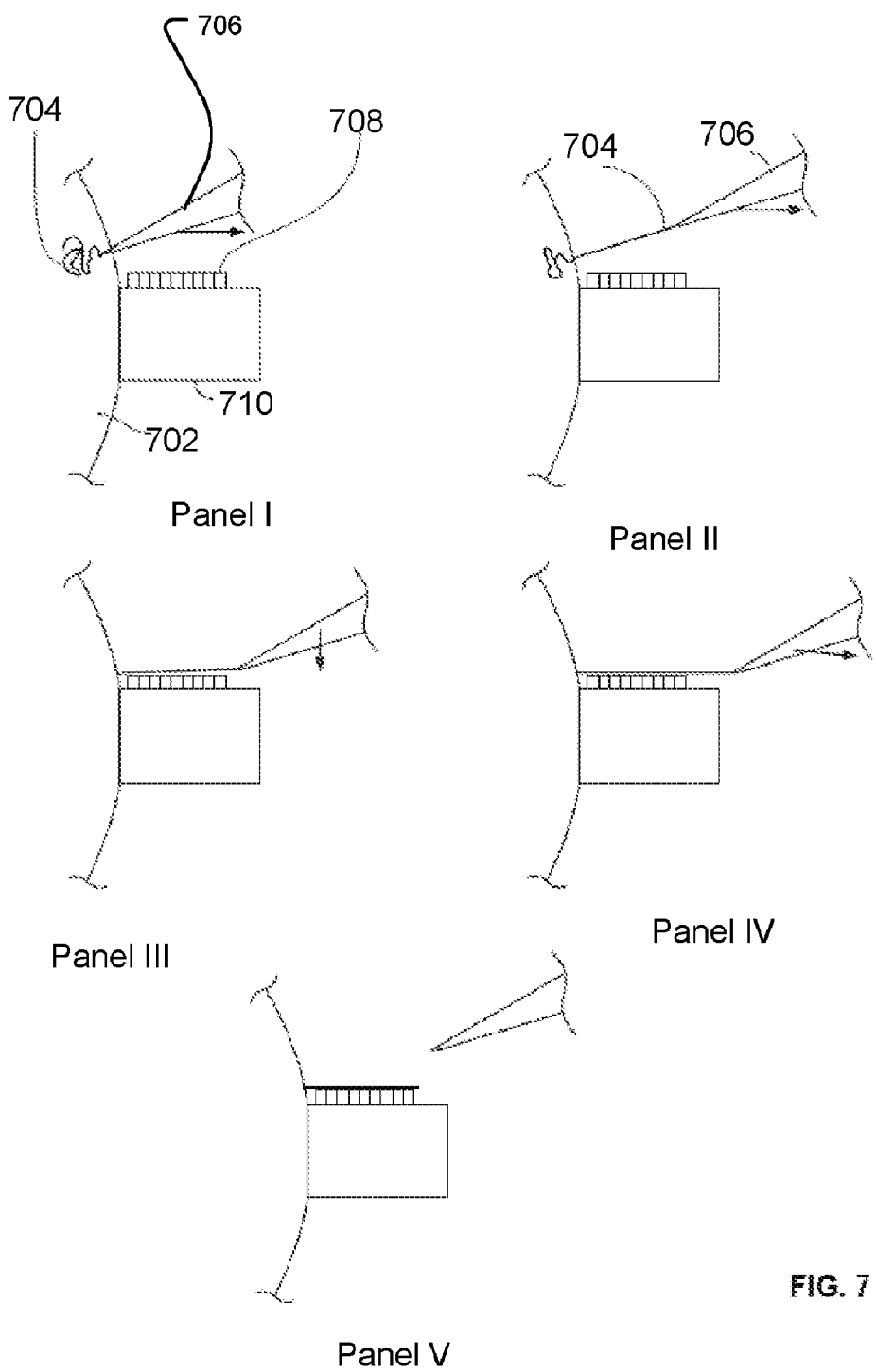
FIG. 7 is a schematic showing the method of shelf threading according to principles of the invention. Panel I shows the sharp needle dipping into the solution containing the labeled nucleic acid strands. Panel II shows the sharp needle withdrawing from the solution and stretching the attached nucleic acid out into empty space. Panel III show the extended nucleic acid coming into contact with the TEM grid. Panels IV and V, show the sharp needle pulling back to release the nucleic acid from the tip of the sharp needle.

In one approach, shelf threading may be employed for placing DNA directly onto an imaging substrate. See FIG. 7, Panels I-V for an illustration. The imaging substrate may support an imaging thin-film that be composed of a material such as single graphene sheets, ultra-thin films of carbon, beryllium oxide or beryllium nitride, water ice (requiring cryo-electron techniques), and other suitable forms of solid low-Z (electron transparent) solids. Since these ultra-thin films are very delicate, they are placed on top of or supported by grid or mesh composed of standard formvar lacey film on a TEM grid, microfabricated holes in SiN membranes (DuraSiN by Protochips, Inc.), or similarly fabricated holey grid. FIG. 7 shows a droplet of solution 702 containing a plurality of labeled nucleic acid strands 704 (only one shown for clarity), a needle 706, a TEM grid 708 on top of a PDMS block 710. As shown in FIG. 7, Panel I, the needle 706 is dipped into the droplet of solution 702. In Panel II, needle 706 is pulled out of solution 702 such that nucleic acid strand 704 is extended out into empty space. In Panel III, extended nucleic acid strand 704 is brought into contact with TEM grid 708. The nucleic acid strand 704 is released from needle 706, as shown in Panels IV-V.

Figure 8:
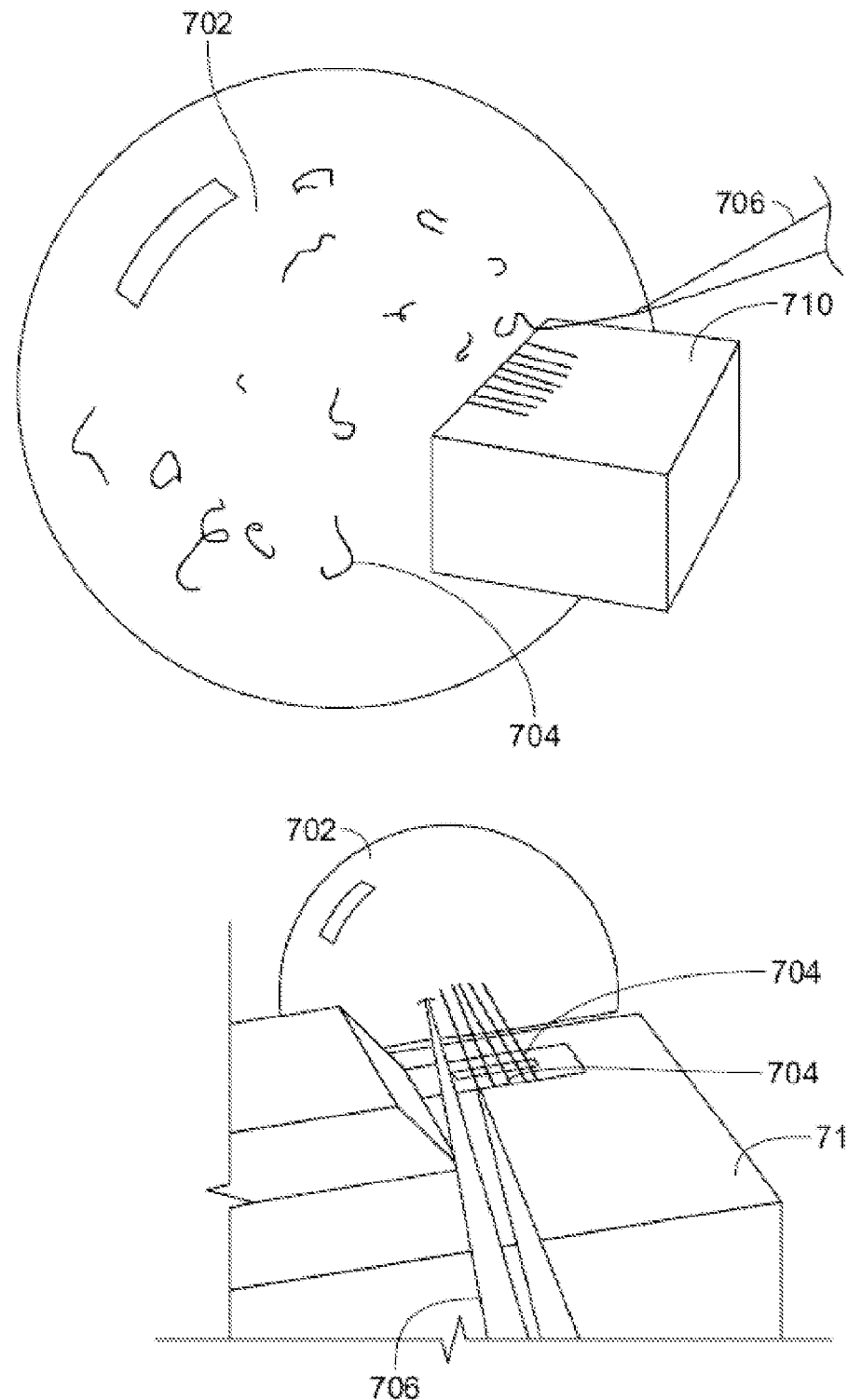
FIG. 8 is schematic representation of the shelf threading method of the invention. Panel I shows shelf threading employing a single needle and Panel II shows shelf threading employing a plurality of needles.

In another approach to shelf threading, illustrated in FIG. 8, the support substrate 710 is placed next to the droplet of nucleic acid polymer solution 702 so that the nucleic acid strand suspended between the droplet and the sharp needle is brought down to contact the support substrate. Then a plurality of nucleic acid strands are transferred to an imaging substrate or by "transfer printing," as described below. FIG. 8, Panel I, schematically illustrates a single needle depositing nucleic acid strands 704 onto a PDMS support substrate 710 and FIG. 8, Panel II schematically illustrates a single needle 706 depositing a plurality of nucleic acid strands 704 onto support film covered, fabricated TEM grid 708, one at a time (shown with the needle in two positions of its motion time-line path).

Figure 9:
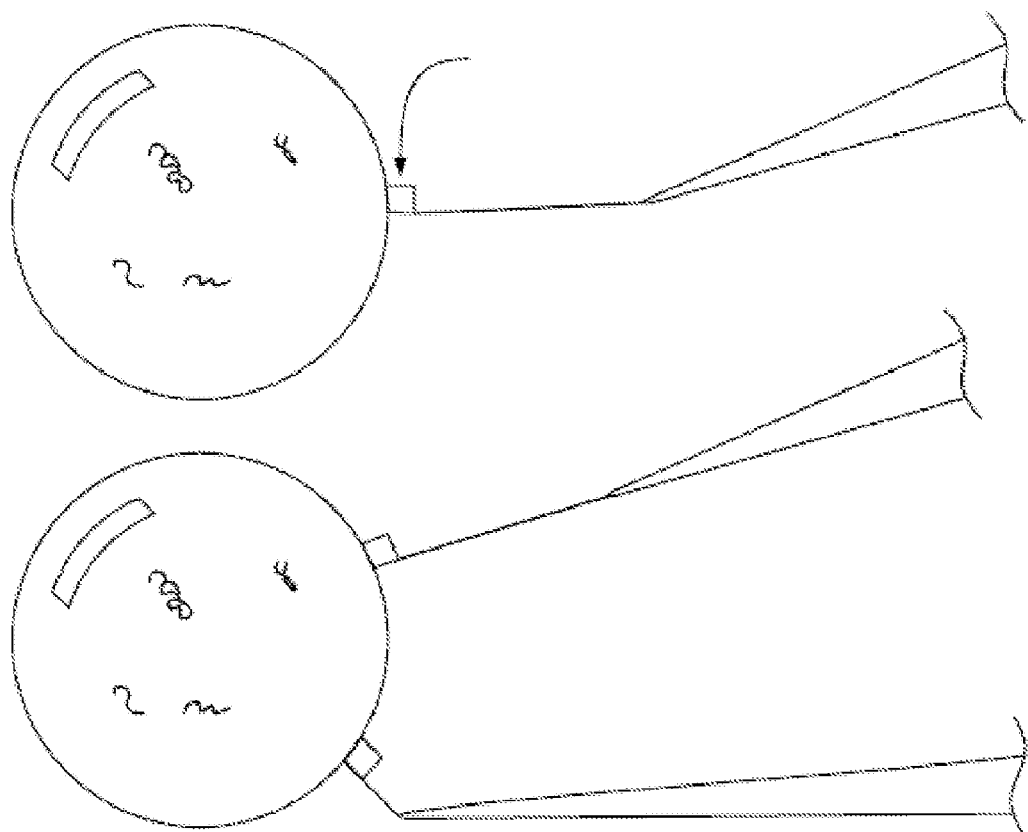
FIG. 9 is a schematic showing that the extended nucleic acid strand is oriented normal to the droplet surface.
Figure 10:
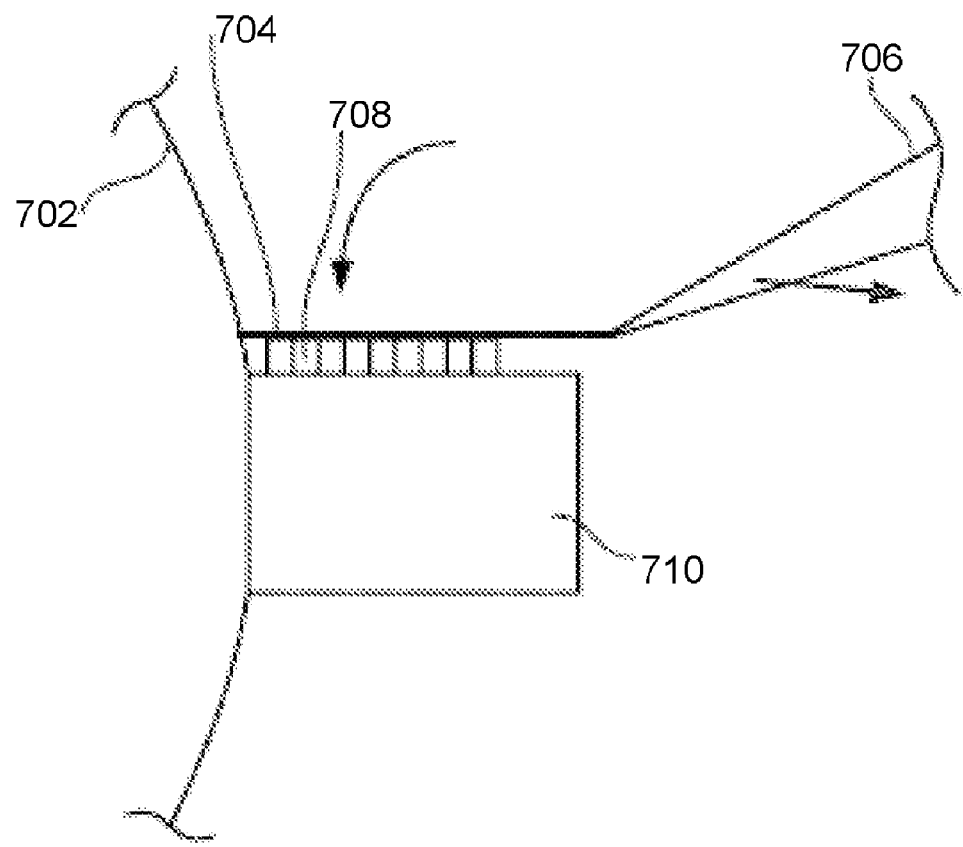
FIG. 10 is a schematic illustrating that the nucleic acid extended in empty space is brought substantially into contact along its length with the support substrate when the strand is placed upon it.
Figure 11:
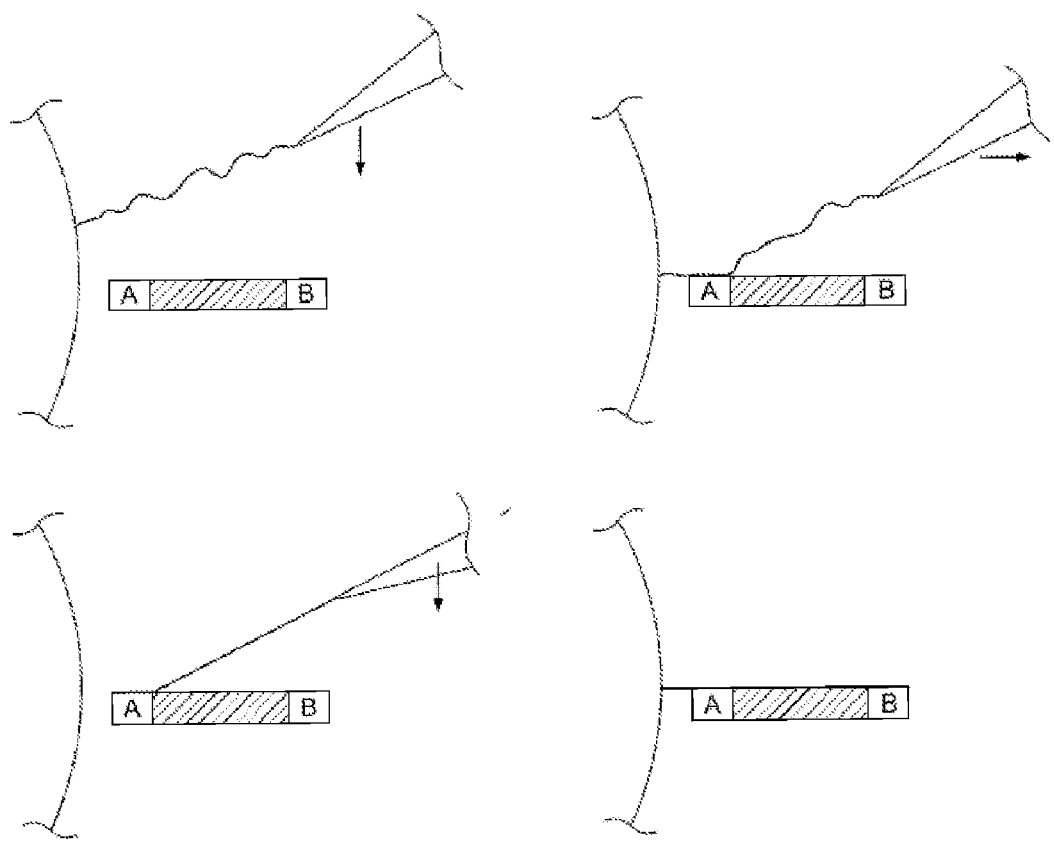
FIG. 11 is a schematic showing elongation of a nucleic acid strand by proximal set down followed by more stretching.

As illustrated in FIG. 9, the nucleic acid strand is always normal to the surface of the droplet. The angle of the solution surface relative to the support substrate and the motion of the needle is controlled such that the nucleic acid 704 in empty space is brought substantially into contact along its length with the substrate 708 when the strand is placed upon it (FIG. 10). The nucleic acid may be elongated after it has been "pulled our of solution. FIG. 11, Panels I-IV, shows elongation of a nucleic acid by proximal setdown followed by more stretching. In FIG. 11, the nucleic acid has exaggerated looseness to illustrate greater stretching by mechanical force than pure meniscus forces. "A" and "B" can represent cross-sectional views of a support such as two bars in an EM grid (on a micro scale) or two strips of PDMS (on a macro scale). "A" and "B" can also represent two positions on a planer substrate.

Figure 13:
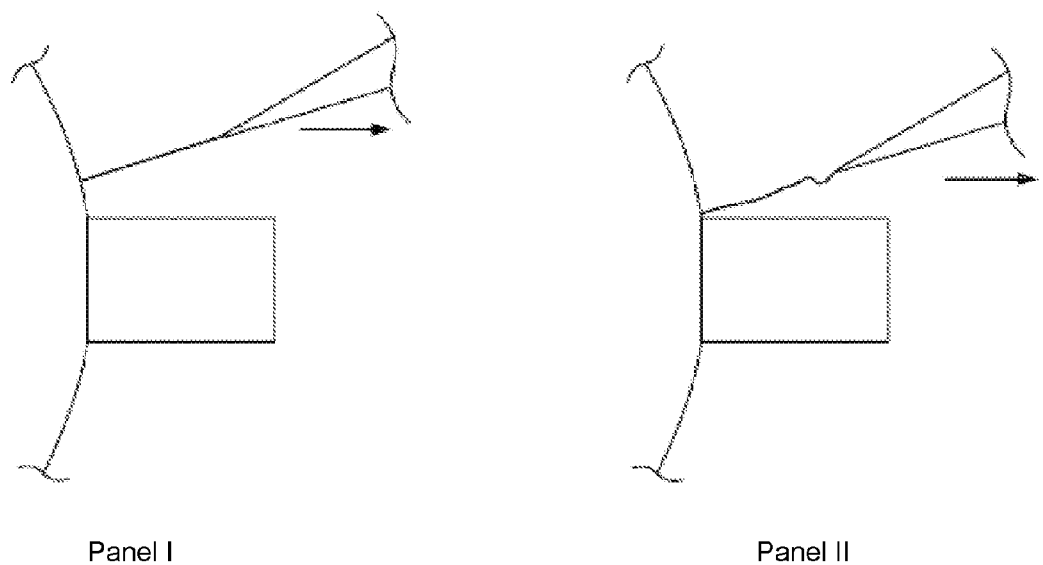
FIG. 13 is a schematic showing a failure mode where improper consideration of solution surface/support substrate/needle motion angles will induce uncontrolled contact between the support substrate and the suspended strand prior to needle-substrate contact, which in turn will cause strand breakage through overstretching
Figure 14:
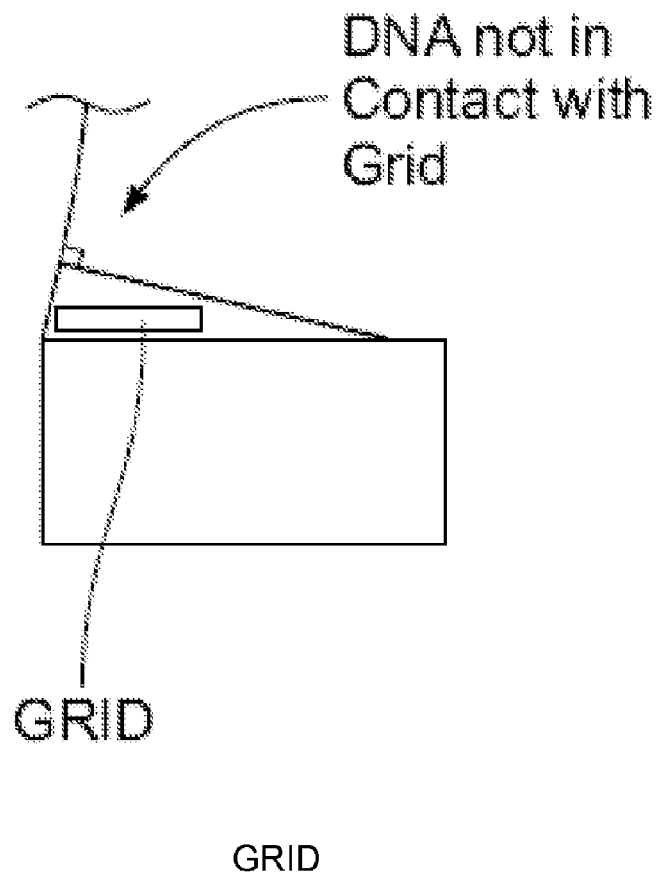
FIG. 14 is a schematic showing a failure mode where wrongly calibrated solution surface/support substrate/needle motion angles will not allow the strand to be brought substantially in contact with the substrate, leaving a significant portion of it suspended in empty space between the solution surface and the point of needle-substrate contact.

FIGS. 13 and 14 illustrate that several parameters may be considered in extending and placing the DNA strands. In one failure mode, improper consideration of solution surface/support substrate/needle motion angles will induce uncontrolled contact between the support substrate and the suspended strand prior to needle-substrate contact, which in turn will cause strand breakage through overstretching (FIG. 13, Panel II). In another failure mode, wrongly calibrated solution surface/support substrate/needle motion angles will not allow the strand to be brought substantially in contact with the substrate, leaving a significant portion of it suspended in empty space between the solution surface and the point of needle-substrate contact (FIG. 14).

Gap Threading

Figure 15:
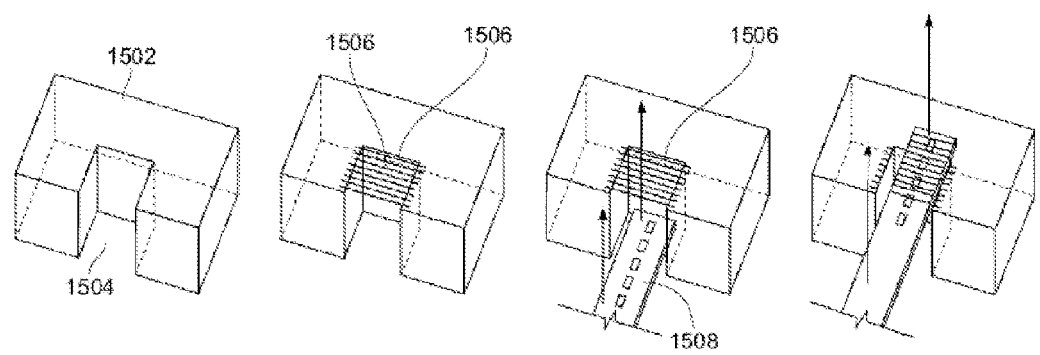
FIG. 15 is a schematic showing the gap threading method according to principles of the invention.

In another embodiment, gap threading may be employed for placing the nucleic acid strands onto the support substrate. Gap threading may be carried out in the following manner, which is illustrated schematically in FIG. 15. FIG. 15 shows a block of PDMS 1502 with gap 1504, nucleic acid strands 1506 spanning across gap 1504, and an imaging substrate—in this case an ultra-flat silicon grid covered with a carbon film or other low Z film 1508. First, the nucleic acid droplet is placed next to a gap in a small block of PDMS. Typically, the PDMS block will have a length of about 3 mm and a width of about 3 mm. The nucleic acid is spanned across the gap by a sharp needle threading as described above. The nucleic acid is spanned across the gap 1504. The ultra-flat silicon grid 1508 covered with a carbon film, holey gold film, or a continuous film of carbon beryllium, other low z film or imaging thin-film (as defined above) is placed in contact with the nucleic acid stretched across gap 1504, causing the nucleic acid to be transferred to the grid 1508 (also referred to as "swipe printing"). As used herein, the term "swipe printing," refers to bringing one or more nucleic acid strands spanning a gap on a support structure into contact with a structure, which may be another support substrate or an imaging substrate or an imaging support thin-film. The block of PDMS 1502 with DNA 1506 spanning the gap 1504 could also be flipped over and transferred to an imaging support film (not shown) by the method of transfer printing, described below.

Transfer Printing

Figure 16:
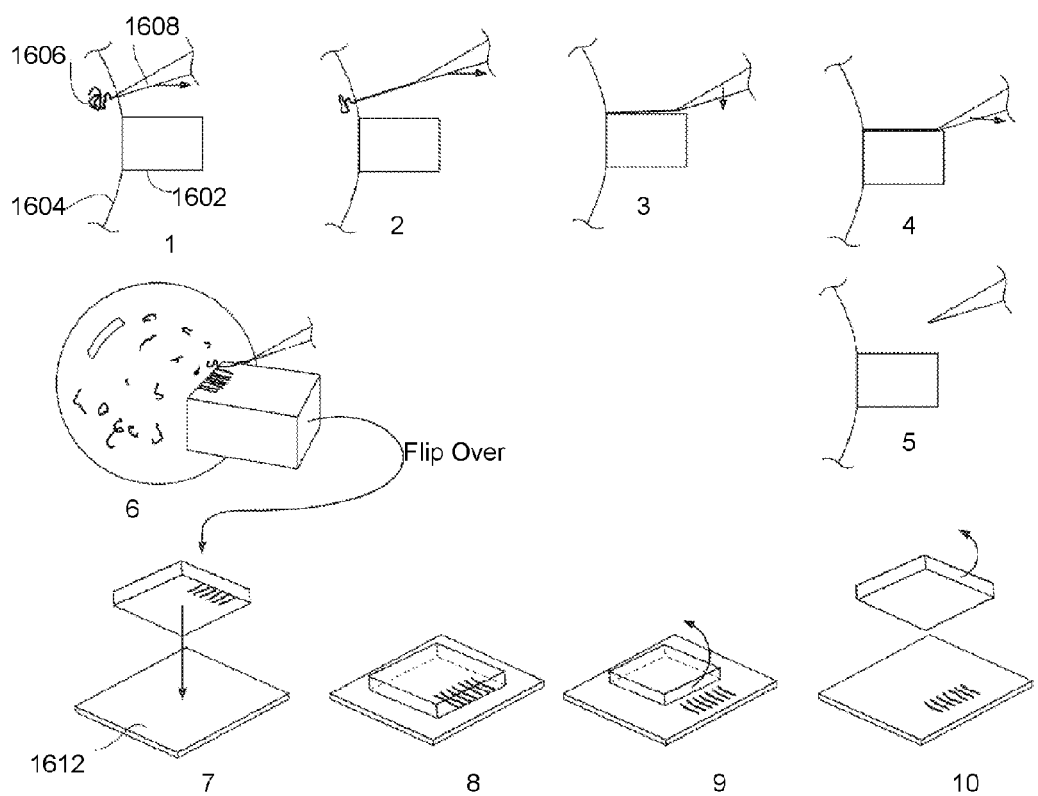
FIG. 16 is a schematic illustrating the transfer printing method according to principles of the invention following deposition of the nucleic acids onto the support substrate.

As discussed above, DNA strands may be placed on a support substrate and subsequently transferred to the imaging substrate or imaging thin-film. One way to do this is by "transfer printing." Transfer printing is known in the filed and is generally described by Nakao, H., ET AL., 125 J. AM. CHEM. SOC. 7162-7163 (2003). Transfer printing may be employed for placing the nucleic acid strands on a support substrate or an imaging support as shown in FIG. 16. FIG. 16 schematically illustrates a block of PDMS 1602 having a length of 3 mm and a width of 3 mm, a droplet 1604 containing nucleic acid 1606, and a needle 1608. The needle 1608 is dipped into the droplet 1604, and a strand of nucleic acid 1606 binds the tip of needle 1608. The needle 1608 is pulled out of droplet 1604, stretching the nucleic acid strand out into empty space. The extended nucleic acid strand 1610 is attached to PDMS block 1602. This process is repeated until a plurality of nucleic acid strands are placed on the PDMS block (Panel 6). Additional care (in the form of greater interstrand-spacing) must be taken so that one threaded strand does not interfere (i.e., touch or cross) with a previously threaded strand. Once the desired number of nucleic acid strands have been placed on the PDMS block 1602, PDMS block 1602 is inverted and placed on an imaging thin-film or other transfer substrate 1612. The PDMS block 1602 is removed from the film 1612, while the DNA stays behind on the film 1612 thereby transferring the plurality of nucleic acid strands to the film 1612. The film can be carbon, beryllium, or other low-z support deposited on a freshly cleaved salt crystal or mica sheet (not shown) when the nucleic acid is transferred and then put on a TEM grid afterwards for imaging.

Alternatively, the nucleic acid strands may be placed onto a support substrate and transferred onto another support substrate for storage, transport, or for other purposes.

The imaging thin film may be an imaging substrate, which is a thin film composed of, without limitation, carbon, boron, beryllium, aluminum, or other low-Z-elements and/or nitrides and oxides thereof, or imaging thin-film as previously defined. These films may be manufactured by known techniques, such as deposition on a cleaved salt crystal or mica. In one specific aspect, an ultra-thin (about 1.5 nm) carbon film is employed. In another aspect, the imaging substrate is an ultra-flat silicon TEM grid that is covered with a thin (about 1.5 nm thick) supporting carbon film. The imaging thin-film may also be placed on a formvar micro-mesh-coated TEM grid or a machined silicon grid with regular or irregular holes or apertures.

In one embodiment, at least one elongated nucleic acid polymer strand may be disposed on a planar substrate. The least one elongated nucleic acid polymer strand may have consistent base-to-base spacing over a length of about 1000 base pairs. A film may be disposed on top of the at least one elongated nucleic acid polymer such that the at least one elongated nucleic acid polymer is sandwiched between the planar substrate and the film. The film may be composed of a carbon or low Z-element. The planar substrate may be composed of a material such as PDMS, carbon, boron, lithium, hydrogen, beryllium, aluminum, nitrides, nitride oxides, and combinations thereof.

The methodology described above is not limited to nucleic acid polymers, but can be used with a wide variety of other long (unbranched) high molecular weight molecules. For example, other high weight polymers including but not limited to nanotubes (e.g., carbon nitrate, boron, boron nitrides, and the like), amino acid chains, microtubules, actin filaments, other long linear polymers with repeating units, and other polymers may be threaded onto a suitable tool and attached to a suitable substrate. In particular, the methods may be used with a linear polymer that binds differentially at its end (terminus) to the needle or other binding tool. In some embodiments the linear molecule may be modified at a terminus or termini so that the end binds preferentially to the tool. For example, the end of the polymer can be complexed to DNA using techniques known by those of skill in the art, which may then bind preferentially at its end to the tool as described above.

Stabilization

Figure 17:
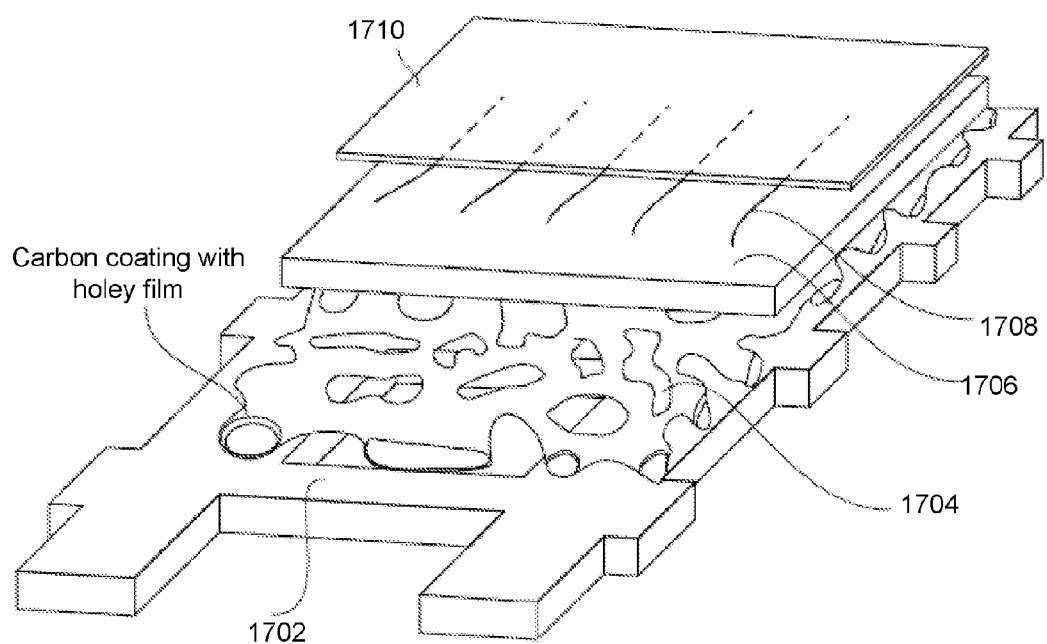
FIG. 17 is a schematic showing the nucleic acid strands on the substrate embedded in top layer prior to imagining by electron microscopy.

The nucleic acid may be damaged by the electron beam generated by the electron microscope. For this reason, in some embodiments, once placed on the imaging substrate the labeled nucleic acid strands may be stabilized prior to imaging. For example, additional carbon or other low-Z-elements or polymers can be placed onto the sample by evaporation, sputtering or direct deposition of a pre-made film. Indirect evaporation of carbon or other low-Z material may be accomplished by ultra-fast PLD-UHV of carbon or beryllium. The presence of this additional layer (i.e., topcoat) increases the stability of the underlying nucleic acid. FIG. 17 schematically illustrates a TEM grid 1702 having a holey mesh 1704, a base layer 1706, nucleic acid 1708, and a top layer 1710.

In one embodiment, the nucleic acid is stabilized by evaporating a topcoat onto the nucleic acid that is made by pulsed laser deposition in a gas atmosphere that cools depositing atoms, but has the conditions of pressure, target to sample distance, pulse length, pulse frequency, and pulse fluence optimized to give a solid homogenous film embedding the labeled nucleic acid polymers. These conditions will cause depositing atoms to have minimum reaction with each other en route to the substrate leading to a denser film fully embedding the labels. The purpose of a topcoat is to stabilize the label and/or DNA in a manner that allows sequence data to be determined, and prevent motion or damage.

The imaging thin-film must be very thin for good images of single atoms to be taken in the TEM. Films that are made by standard techniques often become contaminated after exposure to laboratory air. This contamination build up causes the films to become thicker which can prevent imaging of single atoms and clusters. Besides thickening the film, contaminates from the air can cause structural instabilities of the film when interacting with the electron beam. Rigorous cleanliness and care of the films must be taken to ensure that this buildup does not happen. For all of the methods described herein, all of the steps should preferably be done in a controlled hydrocarbon-free environment (e.g., pure nitrogen, argon, or other inert gasses). Once the DNA has been suspended and or placed on an imaging substrate or transfer substrate like PDMS and removed from solution, all further steps are best continued in a controlled environment, preferably a clean hydrocarbon-free gas, but more preferably UHV ($10^{-10}$ torr). This can include performing threading in a controlled atmosphere environment, placing the DNA stands on the film in UHV, and other cleanliness techniques known to those skilled in the art of nanotechnology, semiconductor manufacturing etc (Krishnan, S.; Laparra, O "Contamination issues in gas delivery for semiconductor processing" Semiconductor Manufacturing, IEEE Transactions on Volume 10, Issue 2, May 1997 Page(s):273-278; William Whyte, Clean room Technology: Fundamentals of Design, Testing and Operation; Dorothy Hoffman, Handbook of Vacuum Science and Technology).

Contamination from the microscope itself is also a key factor that can limit visibility of single atoms. Care must be taken to have a very clean, dry system for imaging. This includes having cold traps, multiple ion pumps, turbo pumps, titanium sublimation pumps, sorption pumps, stage heaters, and load locks (Dorothy Hoffman, Handbook of Vacuum Science and Technology)

Step 112, illustrates and embodiment of the invention, where the labeled nucleic acid on the TEM grid is imaged by electron microscopy. The invention should not be construed to be limited to a TEM grid at this step and may be any imaging substrate known by those of skill in the art. Also, any suitable electron microscope may be used (e.g., a Titan-80-300, Nion UltraSTEM, or VG 501 electron microscope) preferably with suitable aberration correctors using HAADF STEM to visualize the position of the labels.

Figure 18:
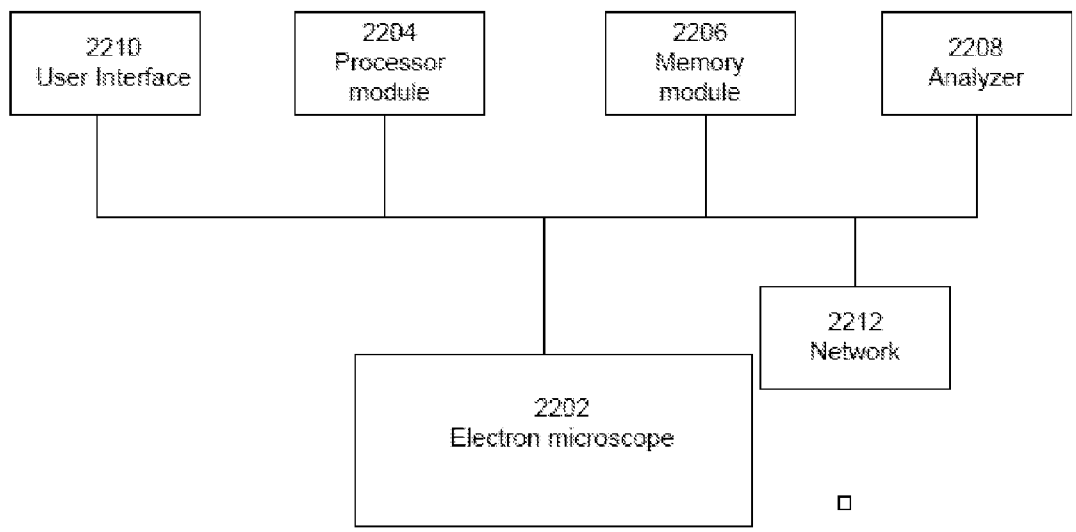
FIG. 18 is a schematic illustrating a system for sequencing a nucleic acid according to principles of the invention.

In step 114, the nucleic acid sequence data is generated and analyzed. According to one embodiment of the invention, FIG. 18 shows a system for analyzing a nucleic acid sequence, which may include an electron microscope 2202, a processor module 2204, at least one memory module 2206, an analyzer module 2208, a user interface 2210, and a network interface 2212. Electron microscope 2202 may be configured to generate an electronic signal representing electron dense regions. Analyzer module 2208 is configured to analyze the nucleic acid sequence based on the electronic signal generated by electron microscope 2202. The at least one memory module 2206 is adapted to stored at least one of the electronic signals representative of the nucleic acid sequence generated by the electron microscope and/or analysis. User interface 2210 is configured to allow the user to interact with the analysis. In a particular embodiment, the at least one memory module includes separate memories for storing the analysis and for storing the electronic signal representing the nucleic acid sequence. In a further embodiment, the analyzer 2208 and the at least on memory module 1806 are remote from the electron microscope and connected to the electron microscope through a network. One or more of the modules are located in the same device, such as a computer or processor to perform the various functions. Alternatively, the modules may be separate pieces of structure to perform the various functions.

Figure 19:
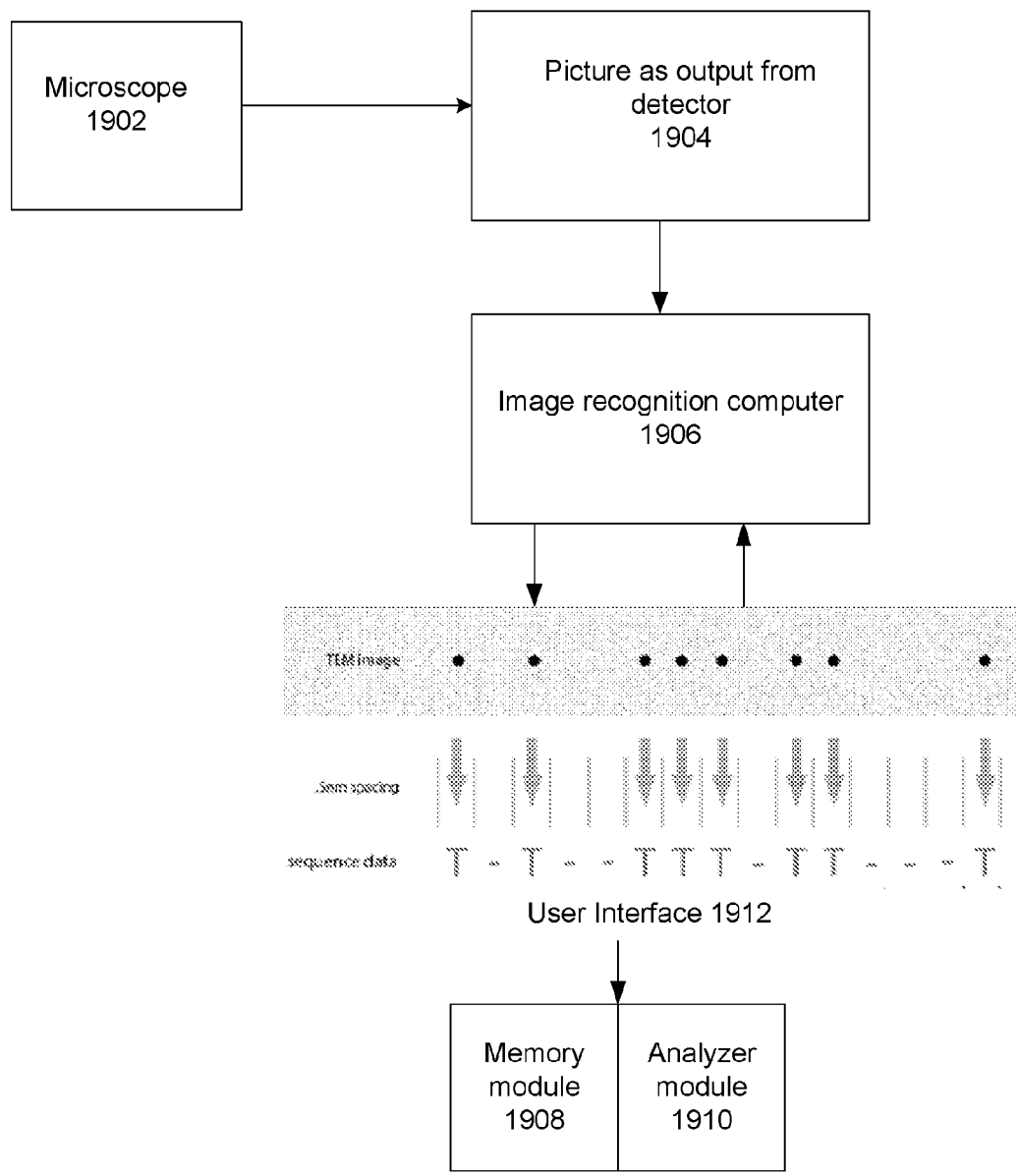
FIG. 19 is a schematic illustrating a hypothetical system for sequencing a nucleic acid according to principles of the invention; a simulated image of a single osmium-labeled molecule of ssDNA generated using principles of the invention.

In a more specific embodiment, data analysis may be collected from a commercially available system or a custom system as shown in FIG. 19. The system in FIG. 19 may include an electronic microscope 1902 (commercially available or a custom microscope), a processor detector 1904, an image recognition computer 1906, at least one memory module 1908, an analyzer module 1910, an user interface 1912 (conceptual view on screen), and an optional network interface (internet or intranet). The electron microscope may be configured to generate an electronic signal representing a nucleic acid sequence. The analyzer module 1910 is configured to analyze the nucleic acid sequence based on the electronic signal generated by electron microscope 1902. In some embodiments memory is a medium selected from hard or floppy disks, optical media, compact disc (CD), digital versatile disc (DVD), semiconductor media, and flash memory.

The final sequence information is assembled either manually or, preferably, using an image recognition system. Nucleic acid spacing information is generated from the high data output detector which may be, for example, a CCD detector, CMOS or PMT. An algorithm is employed to determine from the information received from the high data output CCD detector the spacing of the osmium label, for example, and accordingly, determine the sequence of the specific bases for a given labeling reaction batch. The information received from the CCD is stored on a memory and analyzed. The memory may include e.g., magnetic media such as conventional hard or floppy disks, optical media such as compact disc (CD), digital versatile disc (DVD), or the like, and/or semiconductor media such as flash memory. Algorithms (computer programs) for sequence assembly are well known. Programs that may be used or adapted for use in the invention include, for example, DNA Naser and Cap3, which are the most common sequence assembly software programs used in the art such as those disclosed by U.S. Pat. No. 6,760,668 entitled "Method for Alignment of DNA Sequences with Enhanced Accuracy and Read Length," and U.S. Pat. No. 6,988,039 entitled "Method for Determining Sequence Alignment Significance," the disclosures of which are expressly incorporated herein by reference in their entirety. See also worldwide web at dnabaser.com/index.html (Heracle Software, Lilienthal, Germany); and Huang, X., and Madan, A., 9 GENOME RES. 868-877 (1999). The specific parameters of assembly will depend in part on the nature of the label(s) used. In one embodiment, for example, for each strand imaged, information including the relative position for each labeled base and each unlabeled base is correlated with the specificity of the label (e.g., were all T's labeled, all T's and all C's) to determine the positional sequence for the labeled bases and the information stored. Information stored for a stand and its deduced complement is compared to information generated for other strands and their complements and matches identified. Contiguous sequences are identified and assembled to produce a complete sequence.

When the nucleic acid being sequenced is from a previously sequenced genome (e.g., mouse, human, bacterial, viral) the initial sequence data (e.g., positional sequences within various strands) can be matched to the known reference sequence to accelerate analysis.

In one aspect the invention comprises analyzing a nucleic acid sequence (A's, T's, G's, and C's) stored in a memory, wherein said sequence was determined by the methods described hereinabove. In one aspect the invention comprises receiving imaging data (e.g., the positions of labeled and unlabeled bases), positional sequence (optionally positonal sequence in which at least one base is undetermined) or other sequence information, and processing the data to determine the nucleotide sequence of a nucleic acid sample. Typically the data are received in electronic form. In one embodiment the nucleic acid sequence is genomic sequence of a human subject. In one embodiment the analyzing comprises determining at least one of the presence or absence of one or more single nucleotide polymorphisms, copy number, variants, indels, rearrangements, or whole genome sequences.

A illustrative image of a single stranded DNA strand with Ts labeled is shown in FIG. 19, with a diagram illustrating how the pattern of heavy labels correspond to partial, base-specific sequence information for the area imaged. Information combining multiple imagings of the same underlying sequence with different labels and/or reaction conditions allows for highly accurate sequence determination.

Figure 20:
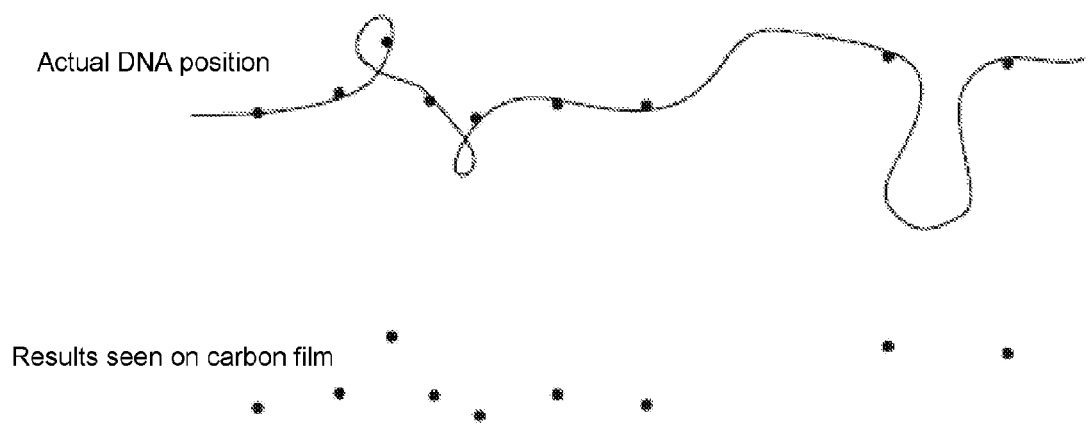
FIG. 20 is a schematic illustrating the ambiguity in images inherent in alternative preparation methods.

The backbone of the nucleic acid does not have to be tracked because the strand is stretched out straight, so that labeling every base with a unique heavy label is not necessary. FIG. 20 illustrates the ambiguity inherent in alternative preparation methods. Using the methods of the invention, described above and in the specific examples, below, phasing errors will not be introduced as a missing label will just be "read" as a blank spot.

Multiple labeling patterns can be combined bioinformatically to determine the underlying nucleic acid sequence. The methods of the invention provide efficiency of throughput as a result of single-molecule placement control. Due to the arrangement of strands in a highly predictable fashion not only individually (i.e., consistent base-to-base spacing) but also predictably parallel dense arrays of single strands, image analysis will be highly efficient. The methods of the invention also allow the stretching force to be controlled, thereby resulting in optimization of the degree of base-to-base spacing.

Without further elaboration, it is believed that one skilled in the art using the preceding description can utilize the invention to the fullest extent. The following examples are illustrative only, and not limiting of the disclosure in any way whatsoever.

EXAMPLES

Example 1

The DNA of interest is isolated from a sample using techniques known to those of ordinary skill in the art. The DNA of interest is then divided into four solutions, i.e., solutions 1, 2, 3, and 4. Each solution is reacted with Os-bipy for different lengths of time and with different concentrations of Os-bipy in order to achieve different base-specific labelling densities.

Solutions 1 and 2 are reacted for 20 hours at 26 degrees Celsius with a four-fold molar excess of Osmium tetroxide and of 2,2'-bipyridine in TE buffer pH 8.0 with 100 mM Tris and 10 mM EDTA; these conditions label about 100% of T's, about 85% of C's, about 7% of G's, and about 0% of A's. Solutions 3 and 4 are reacted under the same conditions as solutions 1 and 2 except that the reaction only proceeds for 15 minutes, and only a 2.5-fold molar excess of Osmium tetroxide and of 2,2'-bipyridine is used; these conditions label about 90% of T's, about 8% of C's, about 5% of G's, and about 0% of A's. However, prior to the Os-bipy reaction, Solutions 2 and 4 are first subjected to a bisulfite treatment to convert unmethylated C residues to U. Bisulfite protocol is known to those skilled in the art, but a very condensed version of such a protocol is described here: Add final concentrations of 0.05 mM hydroquinone, 3.3 M sodium bisulfite, and 3 ng/microliter denatured DNA to a centrifuge tube, cap the tube and shield from light with aluminum foil, incubate at 55 C for 8 hours, purify the DNA by standard methods, and resuspend the DNA in TE buffer (pH 8.0, 100 mM Tris 10 mM EDTA) for subsequent heavy atom labeling. This allows the pattern of methylation to be determined by comparing sequences from solutions treated with bisulfite to those left untreated. According to ref: Jelen ET AL., 10 GEN. PHYS. AND BIOPHYS. at 461. After the labeling reaction, unlabeled osmium is removed by ultrafiltration to minimize extraneous heavy atom contamination during the imaging process and the DNA polymers are diluted to about 0.1 ng/µl in TE buffer pH 8.

A sharp needle is made by heating a glass fiber in an ethanol flame and pulling to separate thereby resulting in two sharp needles with a radii of curvature at their ends of less than about 200 nm. One needle is then coated with PMMA by dipping in a 0.5% solution in acetone and drying in an acetone atmosphere. The needle is then glued on to a holding piece or clamped onto an arm of a positioner such as a piezo actuator (e.g., programmable AFM silicon cantilever) to control the position and motion of the needle.

The needle is dipped into the DNA polymer solution containing the DNA polymers of interest and then pulled out to extend or "pull our the DNA strands into empty space from the DNA polymer solution. The extended DNA polymer strands should remain perpendicular to the surface of the DNA polymer solution.

The DNA polymers are attached to an ultra-flat silicon TEM grid that is covered with a thin carbon film having a thickness in a range of about 1.5 nm to about 5 nm. The silicon TEM grid is made by evaporating carbon on one side of a silicon piece and then etching the back side ensuring that the carbon film is flat using techniques known to those of ordinary skill in the microfabrication industry.

The grid is placed next to the droplet of DNA polymer solution so that the DNA polymer strand suspended between the droplet and the sharp needle is allowed to contact the grid before being completely "pulled out" of the DNA polymer solution. The DNA polymer extended into the empty space is only brought into contact with the TEM grid when the strand is placed on it. Consideration of the angles of the DNA polymer solution with respect to the grid and the motion of the needle is taken to ensure this. Using this threading technique, thousands to millions of strands can be placed parallel to each other on the TEM grid.

The DNA polymer solution is pulled away from the spanning position using a pipette tip or micropositioners moving the base that the droplet rests on. About 0.5 nm to about 6 nm of carbon is then evaporated to stabilize the DNA polymer. The spanning is done in a controlled environment chamber to minimize evaporation and dust.

Imaging is performed in a commercially available Titan 80-300 (FEI Company, Hillsboro, Oreg.) with aberration correctors in Z-contrast STEM mode or other suitable high resolution electron microscope. The information from the detector is used to determine the spacing of the osmium labels and accordingly, the sequence of the DNA of interest.

Example 2

The same methodology is carried out in the same manner as in Specific Example 1, above, with the exception that the DNA polymer is shelf spanned down on a piece of PDMS as shown in FIG. 17. The PDMS is then set in contact with a carbon film on mica so that the DNA polymer is transferred to the carbon. The PDMS piece is then pulled away, leaving the DNA polymer behind. About 1 nm to about 5 nm of carbon is evaporated on top of the DNA polymer on the carbon film on the mica. The carbon film is floated onto water and picked up with a TEM grid. The DNA polymer is then imaged as described in Specific Example 1 or Specific Example 2, to determine the sequence information.

The examples given above are merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in molecular biology, immunology, chemistry, biochemistry or in the relevant fields are intended to be within the scope of the appended claims.

The disclosures of all references and publications cited above are expressly incorporated by reference in their entireties to the same extent as if each were incorporated by reference individually.

What is claimed is:

1. A method of achieving consistent base-to-base spacing in a nucleic acid polymer strand comprising:
    a) introducing a portion of a polymer attachment tool into a solution comprising nucleic acid polymer strands;
    b) attaching a section of at least one strand to the tool;
    c) removing substantially all of the tool with the attached strand from the solution after which at least one region of the strand is suspended between the solution and the tool;
    d) depositing the suspended region of the strand onto a substrate, wherein the strand detaches from the tool; and
    e) obtaining consistent spacing between consecutive bases of the strand.

2. The method of claim 1, wherein the at least one suspended region is suspended between the interface of two surfaces.

3. The method of claim 1, wherein the at least one suspended region is suspended between two phases.

4. The method of claim 1, wherein the at least one suspended region is suspended between an air/solvent interface and the tool.

5. The method of claim 1, wherein the at least one suspended region is suspended between a liquid solution and a solid surface.

6. The method of claim 3, wherein the two phases are selected from the group consisting of a solid, liquid, and gas phase.

7. The method of claim 1, wherein the suspended region of the strand is straightened.

8. The method of claim 1, further comprising placing a plurality of suspended regions on a substrate wherein said suspended regions are substantially parallel to one another.

9. The method of claim 8, wherein the suspended regions do not overlap with one another on the substrate.

10. The method of claim 1, wherein the spacing between consecutive bases in the suspended region ranges from 3 angstroms to 7 angstroms.

11. The method of claim 1, wherein the tool is configured to attach to multiple strands.

12. The method of claim 1, wherein the polymer attachment tool is a needle.

13. The method of claim 12, wherein the tool is a needle array.

14. The method of claim 1, wherein the tool is capable of attaching to multiple regions on a single strand.

15. The method of claim 1, wherein the suspended region is at least 20 nanometers in length.

16. The method of claim 1, wherein the suspended region is at least 100 microns in length.

17. The method of claim 16, wherein the base pairs in the suspended region do not overlap.

18. The method of claim 1, wherein the tool manipulates the strand while the strand is in solution.

19. The method of claim 1, wherein the nucleic acid polymer strands comprise single stranded nucleic acid strands.

20. The method of claim 1, wherein the nucleic acid polymer strands comprise double stranded nucleic acid strands.

21. A method of achieving consistent base-to-base spacing in a nucleic acid strand, comprising:
    a) introducing a portion of a polymer attachment tool into a solution comprising nucleic acid polymer strands;
    b) attaching a section of at least one strand to the tool;
    c) removing substantially all of the tool with the attached strand from the solution after which at least one region of the strand is suspended between the solution and the tool;
    d) depositing the suspended region of the strand onto a substrate, wherein the substrate is distinct from the polymer attachment tool;
    e) obtaining consistent spacing between consecutive bases of the strand.

22. A method of sequencing a labeled nucleic acid polymer strand, comprising:
    a) introducing a portion of a polymer attachment tool into a solution comprising nucleic acid polymer strands;
    b) attaching a strand to the tool;
    c) removing substantially all of the tool with the attached strand from the fluid after which at least one suspended region of the strand is suspended between the fluid and the tool;
    d) obtaining consistent spacing between consecutive bases in said suspended region of the strand:
    e) placing the strand on a substrate wherein the substrate is distinct from the polymer attachment tool and such that the consistent spacing is substantially preserved;
    f) imaging the strand with an electron microscope (EM) to produce EM data: and
    g) determining the base sequence for substantially the entire strand from the EM data;
    wherein at least a subset of the bases of the strand are associated with a label that is resolvable by an electron microscope.

23. The method of claim 22, wherein the label is a contrast agent label.

24. The method of claim 23, wherein the contrast agent is a high-Z-atom labeling compound.

25. The method of claim 22, wherein the label is a cluster label.

26. The method of claim 23, wherein the contrast agent directly labels the nucleic acid polymer strand.

27. The method of claim 22, wherein the bases are associated with a single label type.

28. The method of claim 22, wherein the bases are associated with a single label type under two different reaction conditions 29. The method of claim 22, wherein the bases are associated with two label types.

30. The method of claim 22, wherein the imaging step determines the location of bases associated with labels and bases not associated with labels.

31. The method of claim 22, wherein the nucleic acid polymer strand is a DNA strand.

32. The method of claim 31, wherein thymine and cytosine are selectively associated with labels while adenine and guanine are not, significantly, associated with labels.

33. The method of claim 31, wherein only the guanine bases are, significantly, associated with labels.

34. The method of claim 32, wherein only the thymine bases are, significantly, associated with labels.

35. The method of claim 32, wherein only the adenine bases are, significantly, associated with labels.

36. The method of claim 32, wherein only the uracil bases are, significantly, associated with labels.

37. The method of claim 32, wherein only the cytosine bases are, significantly, associated with labels.

* * * * *